(12) United States Patent
Collins et al.

(10) Patent No.: US 7,670,596 B2
(45) Date of Patent: Mar. 2, 2010

(54) MULTI-LINEAGE PROGENITOR CELLS

(75) Inventors: Daniel P. Collins, Lino Lakes, MN (US); Stacey L. Sprague, Woodbury, MN (US); Barbara M. Tigges, Hudson, WI (US)

(73) Assignee: BioE, Inc., St. Paul, MN (US)

( * ) Notice: Subject to any disclaimer, the term of this patent is extended or adjusted under 35 U.S.C. 154(b) by 656 days.

(21) Appl. No.: 11/110,299

(22) Filed: Apr. 20, 2005

(65) Prior Publication Data

US 2005/0255592 A1 Nov. 17, 2005

Related U.S. Application Data

(60) Provisional application No. 60/564,687, filed on Apr. 23, 2004.

(51) Int. Cl.
*A01N 63/00* (2006.01)
*A61K 8/18* (2006.01)
*A01N 1/02* (2006.01)
*C12Q 1/37* (2006.01)
*C12N 5/00* (2006.01)

(52) U.S. Cl. .................. 424/93.1; 424/93.73; 435/2; 435/7.23; 435/7.24; 435/7.25; 435/325; 435/355; 436/523

(58) Field of Classification Search ................ 424/93.1, 424/93.7, 3; 435/2, 7.23, 7.24, 7.25, 325, 435/355; 436/523
See application file for complete search history.

(56) References Cited

U.S. PATENT DOCUMENTS

| | | | |
|---|---|---|---|
| 5,004,681 A | 4/1991 | Boyse et al. |
| 5,130,144 A | 7/1992 | Civin |
| 5,192,553 A | 3/1993 | Boyse et al. |
| 5,453,357 A | 9/1995 | Hogan |
| 5,486,359 A | 1/1996 | Caplan et al. |
| 5,580,714 A | 12/1996 | Polovina |
| 5,624,840 A | 4/1997 | Naughton et al. |
| 5,744,347 A | 4/1998 | Wagner et al. |
| 5,750,397 A | 5/1998 | Tsukamoto et al. |
| 5,789,147 A | 8/1998 | Rubinstein et al. |
| 5,827,735 A | 10/1998 | Young et al. |
| 5,827,740 A | 10/1998 | Pittenger |
| 5,830,651 A | 11/1998 | Cauley et al. |
| 5,843,780 A | 12/1998 | Thomson |
| 5,877,299 A | 3/1999 | Thomas et al. |
| 5,908,782 A | 6/1999 | Marshak et al. |
| 5,928,214 A | 7/1999 | Rubinstein et al. |
| 5,942,225 A | 8/1999 | Bruder et al. |
| 5,965,436 A | 10/1999 | Thiede et al. |
| 5,968,829 A | 10/1999 | Carpenter |
| 6,030,836 A | 2/2000 | Thiede et al. |
| 6,103,530 A | 8/2000 | Carpenter |
| 6,140,121 A | 10/2000 | Ellington et al. |
| 6,200,806 B1 | 3/2001 | Thomson |
| 6,251,669 B1 | 6/2001 | Luskin |
| 6,280,718 B1 | 8/2001 | Kaufman et al. |
| 6,306,575 B1 | 10/2001 | Thomas et al. |
| 6,322,784 B1 | 11/2001 | Pittenger et al. |
| 6,328,960 B1 | 12/2001 | McIntosh et al. |
| 6,387,367 B1 | 5/2002 | Davis-Sproul et al. |
| 6,432,711 B1 | 8/2002 | Dinsmore et al. |
| 6,436,704 B1 | 8/2002 | Roberts et al. |
| 6,448,075 B1 | 9/2002 | Thomas et al. |
| 6,461,645 B1 | 10/2002 | Boyse et al. |
| 6,465,247 B1 | 10/2002 | Weissman et al. |
| 6,477,090 B2 | 11/2002 | Yamaki et al. |
| 6,482,926 B1 | 11/2002 | Thomas et al. |
| 6,491,917 B1 | 12/2002 | Thomas et al. |
| 6,491,918 B1 | 12/2002 | Thomas et al. |
| 6,498,034 B1 | 12/2002 | Strobl |
| 6,569,427 B1 | 5/2003 | Boyse et al. |
| 6,605,275 B1 | 8/2003 | Boyse et al. |
| 6,645,727 B2 | 11/2003 | Thomas et al. |
| 6,680,198 B1 | 1/2004 | Snyder et al. |
| 6,709,864 B1 | 3/2004 | Pittenger et al. |
| 6,740,493 B1 | 5/2004 | Long et al. |
| 6,750,326 B2 | 6/2004 | Thomas et al. |
| 6,761,883 B2 | 7/2004 | Weissman et al. |
| 6,767,737 B1 | 7/2004 | Wilson et al. |
| 6,777,231 B1 | 8/2004 | Katz et al. |
| 6,777,233 B2 | 8/2004 | Carpenter |
| 6,800,480 B1 | 10/2004 | Bodnar et al. |
| 6,835,377 B2 | 12/2004 | Goldberg et al. |
| 6,852,533 B1 | 2/2005 | Rafii et al. |
| 6,875,430 B2 | 4/2005 | McIntosh et al. |
| 6,887,704 B2 | 5/2005 | Peled et al. |
| 6,911,201 B1 | 6/2005 | Merchav et al. |
| 6,946,293 B1 | 9/2005 | Lu et al. |
| 6,962,698 B1 | 11/2005 | Peled et al. |
| 6,967,086 B2 | 11/2005 | Guarino et al. |
| 6,986,887 B2 | 1/2006 | Lawman et al. |
| 6,991,897 B2 | 1/2006 | Smith et al. |
| 7,015,037 B1 | 3/2006 | Furcht et al. |
| 7,045,148 B2 | 5/2006 | Hariri |
| 7,122,178 B1 | 10/2006 | Simmons et al. |
| 7,160,723 B2 | 1/2007 | Collins et al. |
| 7,255,879 B2 | 8/2007 | Hariri |

(Continued)

FOREIGN PATENT DOCUMENTS

EP  03017676.2  *  8/2003

(Continued)

OTHER PUBLICATIONS

Madlambayan GJ, Rogers I, Casper RF, Zandstra PW. 2001. Controlling culture dynamics for the expansion of hematopoietic stem cells. J Hematother Stem Cell Res. 10(4):481-92.*

(Continued)

*Primary Examiner*—Maria Leavitt
(74) *Attorney, Agent, or Firm*—Fish & Richardson P.C.

(57) ABSTRACT

Fetal blood multi-lineage progenitor cells that are capable of a wide spectrum of transdifferentiation are described.

36 Claims, 2 Drawing Sheets

U.S. PATENT DOCUMENTS

| | | |
|---|---|---|
| 7,399,632 B2 | 7/2008 | Simmons et al. |
| 7,413,734 B2 | 9/2008 | Mistry et al. |
| 7,470,537 B2 | 12/2008 | Hedrick et al. |
| 7,473,420 B2 | 1/2009 | Fraser et al. |
| 2001/0034061 A1 | 10/2001 | Csete et al. |
| 2001/0046489 A1 | 11/2001 | Habener et al. |
| 2002/0012903 A1 | 1/2002 | Goldman et al. |
| 2002/0028510 A1 | 3/2002 | Sanberg et al. |
| 2002/0045196 A1 | 4/2002 | Mahoney et al. |
| 2002/0064519 A1 | 5/2002 | Bruder et al. |
| 2002/0068045 A1 | 6/2002 | Reubinoff et al. |
| 2002/0132987 A1 | 9/2002 | Anderson |
| 2002/0164308 A1 | 11/2002 | Reubinoff et al. |
| 2002/0164790 A1 | 11/2002 | Warburton et al. |
| 2002/0164794 A1 | 11/2002 | Wernet |
| 2002/0168763 A1 | 11/2002 | Yan et al. |
| 2002/0177227 A1 | 11/2002 | Kraus et al. |
| 2002/0192816 A1 | 12/2002 | Roberts et al. |
| 2003/0003084 A1 | 1/2003 | Seshi |
| 2003/0027233 A1 | 2/2003 | Collins et al. |
| 2003/0032179 A1 | 2/2003 | Hariri |
| 2003/0092078 A1 | 5/2003 | Thomas et al. |
| 2003/0113910 A1* | 6/2003 | Levanduski ............... 435/325 |
| 2003/0134416 A1 | 7/2003 | Yamanishi et al. |
| 2003/0157078 A1 | 8/2003 | Hall et al. |
| 2003/0161818 A1 | 8/2003 | Weiss et al. |
| 2003/0165852 A1 | 9/2003 | Schueler et al. |
| 2003/0180269 A1* | 9/2003 | Hariri ..................... 424/93.21 |
| 2003/0203483 A1 | 10/2003 | Seshi |
| 2003/0235563 A1 | 12/2003 | Strom et al. |
| 2003/0235909 A1 | 12/2003 | Hariri et al. |
| 2004/0018621 A1 | 1/2004 | Reid et al. |
| 2004/0028660 A1 | 2/2004 | Hariri et al. |
| 2004/0058398 A1 | 3/2004 | Sarvetnick et al. |
| 2004/0058412 A1 | 3/2004 | Ho et al. |
| 2004/0107453 A1 | 6/2004 | Furcht et al. |
| 2004/0121464 A1 | 6/2004 | Rathjen et al. |
| 2004/0137612 A1 | 7/2004 | Baksh et al. |
| 2004/0142463 A1 | 7/2004 | Walker et al. |
| 2004/0161419 A1 | 8/2004 | Strom et al. |
| 2004/0171147 A1 | 9/2004 | Hariri |
| 2004/0203142 A1 | 10/2004 | Rai |
| 2004/0219136 A1 | 11/2004 | Hariri |
| 2004/0228847 A1 | 11/2004 | Goldschmidt-Clermont et al. |
| 2004/0259254 A1 | 12/2004 | Honmou et al. |
| 2005/0019865 A1 | 1/2005 | Kihm et al. |
| 2005/0019908 A1 | 1/2005 | Hariri |
| 2005/0019911 A1 | 1/2005 | Gronthos et al. |
| 2005/0032209 A1 | 2/2005 | Messina et al. |
| 2005/0037493 A1 | 2/2005 | Mandalam et al. |
| 2005/0048035 A1 | 3/2005 | Fraser et al. |
| 2005/0053588 A1 | 3/2005 | Yin |
| 2005/0054098 A1 | 3/2005 | Mistry et al. |
| 2005/0058629 A1 | 3/2005 | Harmon et al. |
| 2005/0058630 A1 | 3/2005 | Harris et al. |
| 2005/0058631 A1 | 3/2005 | Kihm et al. |
| 2005/0059147 A1 | 3/2005 | Seshi |
| 2005/0063961 A1 | 3/2005 | Friedlander et al. |
| 2005/0074435 A1 | 4/2005 | Casper et al. |
| 2005/0095703 A1 | 5/2005 | Semb et al. |
| 2005/0106554 A1 | 5/2005 | Palecek et al. |
| 2005/0118715 A1 | 6/2005 | Hariri |
| 2005/0124003 A1 | 6/2005 | Atala et al. |
| 2005/0142118 A1 | 6/2005 | Wernet |
| 2005/0158289 A1 | 7/2005 | Simmons et al. |
| 2005/0176139 A1 | 8/2005 | Chen et al. |
| 2005/0181502 A1 | 8/2005 | Furcht et al. |
| 2005/0255592 A1 | 11/2005 | Collins et al. |
| 2005/0260748 A1 | 11/2005 | Chang et al. |
| 2005/0260751 A1 | 11/2005 | Lucas et al. |
| 2006/0008450 A1 | 1/2006 | Verfaillie et al. |
| 2006/0030039 A1 | 2/2006 | Chen et al. |
| 2006/0037092 A1 | 2/2006 | Lawman et al. |
| 2006/0040392 A1 | 2/2006 | Collins et al. |
| 2006/0078993 A1 | 4/2006 | Phan et al. |
| 2006/0134636 A1 | 6/2006 | Stanton et al. |
| 2006/0154366 A1 | 7/2006 | Brown et al. |
| 2006/0182724 A1 | 8/2006 | Riordan |

FOREIGN PATENT DOCUMENTS

| | | |
|---|---|---|
| WO | WO 90/11354 | 10/1990 |
| WO | WO 91/01140 | 2/1991 |
| WO | WO 93/04169 | 3/1993 |
| WO | 02/36751 | 5/2002 |
| WO | WO 02/083262 | 10/2002 |
| WO | 03/055989 | 7/2003 |
| WO | WO 03/068937 | 8/2003 |
| WO | 03/078610 | 9/2003 |
| WO | 2004/024875 | 3/2004 |
| WO | 2004/029208 | 4/2004 |
| WO | WO 2005/071732 | 2/2005 |

OTHER PUBLICATIONS

Belov et al., Immunophenotyping of leukemias using a cluster of differentiation antibody microarray.Cancer Res. Jun. 1, 2001;61(11):4483-9.*

Lodie et al., Systematic analysis of reportedly distinct populations of multipotent bone marrow-derived stem cells reveals a lack of distinction.Tissue Eng. Oct. 2002;8(5):739-51.*

Tocci et al., Mesenchymal stem cell: use and perspectives. Hematol J. 2003;4(2):92-6.*

U.S. Appl. No. 60/335,878, filed Nov. 15, 2001, Atala.

U.S. Appl. No. 60/356,295, filed Feb. 13, 2002, Atala.

Bradley, "Modifying the mammalian genome by gene targeting," *Curr. Opin. Biotechnol.*, 1991, 2:823-829.

Eggens et al., "Specific Interaction between Le$^x$ and Le$^x$ Determinants. A Possible Basis for Cell Recognition in Preimplantation Embryos and in Embryonal Carcinoma Cells," *J. Biol. Chem.*, 1989, 264(16):9476-9484.

Fowler and Greenspan, "Application of Nile Red, a Fluorescent Hydrophobic Probe, for the Detection of Neutral Lipid Deposits in Tissue Sections: Comparison with Oil Red O," *J. Histochem. Cytochem.*, 1985, 33(8):833-836.

Jaiswal et al., "Osteogenic Differentiation of Purified, Culture-Expanded Human Mesenchymal Stem Cells In Vitro," *J. Cell. Biochem.*, 1997, 64(2):295-312.

Jennings et al., "CD9 cluster workshop report: cell surface binding and functional analysis," *Leucocyte Typing V*, 1995, Schlossmann et al. (eds.), Oxford University Press, Oxford, pp. 1249-1251.

Johnson et al., "Bone marrow may be source of new egg-cell generation in adult mammals," [online] 2005, [retrieved on 200-07-29]. Retrieved from the Internet: <URL: www.eurekalert.org/pub‾releases/2005-07/mgh-bmm071505.php>.

Kannagi et al., "A Series of Human Erythrocyte Glycosphingolipids Reacting to the Monoclonal Antibody Directed to a Developmentally Regulated Antigen, SSEA-1," *J. Biol. Chem.*, 1982, 257:14865.

Kay et al., "Gene therapy," *Proc. Natl. Acad. Sci. USA*, 1997, 94:12744-12746.

Lanza et al., "cDNA cloning and expression of platelet p24/CD9. Evidence for a new family of multiple membrane-spanning proteins," *J. Biol. Chem.*, 1991, 266(16):10638-10645.

Magnani et al., "Monoclonal Antibodies PMN 6, PMN 29, and PM-81 Bind Differently to Glycolipids Containing a Sugar Sequence Occurring in Lacto-$N$-Fucopentaose III," *Arch. Biochem. Biophys.*, 1984, 233(2):501-506.

Outram et al., "Erythromyeloid Lineage Fidelity is Conserved in Erythroleukaemia," *Leukemia Research*, 1988, 12(8):651-657.

Pittenger et al., *Science*, 1999, 284:143-147.

Reinberg, "Banking on Stem Cells," [online]. The Scientist, 2005, [retrieved on Jul. 28, 2005]. Retrieved from the Internet: <URL: www.the-scientist.com>.

Rubinstein et al., "Anti-Platelet Antibody Interactions with Fcγ Receptor," *Semin. Thromb. Hemost.*, 1995, 21:10-22.

Solter et al., "Monoclonal antibody defining a stage-specific mouse embryonic antigen (SSEA-1)," *Proc. Natl. Acad. Sci. USA*, 1978, 75(11):5565-5569.

Telen and Bolk, "Human red cell antigens. IV. The abnormal sialoglycoprotein of Gerbich-negative red cells," *Transfusion*, 1987, 27:309-314.

Bigbee et al., "Monoclonal antibodies specific for the M- and N-forms of human glycophorin A," *Mol. Immunol.*, 1983, 20(12):1353-1362.

Von dem Borne and Modderman, *Leucocyte Typing IV*, 1989, Knapp et al. (eds.), Oxford University Press, Oxford, pp. 989-992.

Wright and Tomlinson, "The ins and outs of the transmembrane 4 superfamily," *Immunology Today*, 1994, 15(12):588-594.

Forraz et al., "Haemopoietic and neuroglial progenitors are promoted during cord blood ex vivo expansion," *Br. J. Haematol.*, 2002, 119:888.

Forraz et al., "Characterization of a Lineage-Negative Stem-Progenitor Cell Population Optimized for Ex Vivo Expansion and Enriched for LTC-IC," *Stem Cells*, 2004, 22:100-108.

Forraz et al., "AC133+umbilical cord blood progenitors demonstrate rapid self-renewal and low apoptosis," *Br. J. Haematol.*, 2002, 119:516-524.

Kögler et al., "A New Human Somatic Stem Cell from Placental Cord Blood with Intrinsic Pluripotent Differentiation Potential," *J. Exp. Med.*, 2004, 200(2):123-135.

McGuckin et al., "Production of stem cells with embryonic characteristics from human umbilical cord blood," *Cell Prolif.*, 2005, 38:245-255.

McGuckin et al., "Multiparametric analysis of immature cell populations in umbilical cord blood and bone marrow," *Eur. J. Haematol.*, 2003, 71:341-350.

McGuckin et al., "Umbilical cord blood stem cells can expand hematopoietic and neuroglial progenitors in vitro," *Exp. Cell Res.*, 2004, 295:350-359.

McGuckin et al., "Colocalization Analysis of Sialomucins CD34 and CD164," *Stem Cells*, 2003, 21:162-170.

McGuckin et al., "Thrombopoietin, flt3-ligand and c-kit-ligand modulate *HOX* gene expression in expanding cord blood CD133+cells," *Cell Prolif.*, 2004 37:295-306.

Perez et al., "Human Cord Blood derived Stem Cells Differentiated into Hormone-Expressing Islet Cell-like Aggregates to Produce Insulin as an Alternative to Pancreatic transplant for diabetic and pancreatic Cancer Patients," http://www.eliondiagnostics.com/pdf/news/Celprogen_Stem_ Cell_Abstract.pdf#search=%22perez%20pancreatic%20cord%20blood%22, Stem Cells Research and Therapeutics Conference, San Diego, CA, Apr. 11 and 12, 2005, 4 pages.

Whiting et al., "Three-dimensional analysis of CD34 sialomucin distribution on cord blood and bone marrow," *Br. J. Haematol.*, 2003, 122:771-777.

Xiao et al., "Transplantation of a Novel Cell Line Population of Umbilical Cord Blood Stem Cells Ameliorates Neurological Deficits Associated with Ischemic Brain Injury," *Stem Cells Dev.*, 2005, 14:722-733.

Yoon et al., "Clonally expanded novel multipotent stem cells from human bone marrow regenerate myocardium after myocardial infarction," *J. Clin. Invest.*, 2005, 115:326-338.

Goodwin et al., "Multilineage Differentiation Activity by Cells Isolated From Umbilical Cord Blood: Expression of Bone, Fat, and Neural Markers," *Biol. Blood Marrow Transplant.*, 2001, 7:581-588.

Lam et al., "Preclinical ex vivo expansion of cord blood hematopoietic stem and progenitor cells: duration of culture; the media, serum supplements, and growth factors used; and engraftment in NOD/SCID mice," *Transfusion*, 2001, 41:1567-1576.

Rutella et al., "Identification of a Novel Subpopulation of Human Cord Blood CD34−CD133−CD7−CD45+Lineage− Cells Capable of Lymphoid/NK Cell Differentiation After In Vitro Exposure to IL-15," *J. Immunol.*, 2003, 171:2799-2988.

Berger et al. "Differentiation of umbilical cord blood-derived multilineage progenitor cells into respiratory epithelial cells." *Cytotherapy*. 2006, 8(5):480-487.

Hou et al. "Study of in vitro expansion and differentiation into neuron-like cells of human umbilical cord blood mesenchymal stem cells" *Chin J. Hematology*. 2002: 23(8): 414-419.

Jager et al. "Antigen expression of cord blood derived stem cells under osteogenic stimulation in vitro" *Cell Biology International*. 2007, 31:950-957.

Kobune et al. "Telomerized human multipotent mesenchymal cells can differentiate into hematopoietic and cobblestone area—supporting cells" *Experimental Hematology*. 2003, 31: 715-722.

U.S. Appl. No. 11/452,502, filed Jun. 14, 2006, Collins.

U.S. Appl. No. 11/736,273, filed Apr. 17, 2007, McKenna, Jr. et al.

U.S. Appl. No. 60/951,885, filed Jul. 25, 2007, Collins.

Kogler et al. "Cytokine production and hematopoiesis supporting activity of cord blood—derived unrestricted somatic stem cells"*Experimental Hematology*. 2005 , 33:573-583.

Lakshmipathy et al, "Efficient Transfection of Embryonic and Adult Stem Cells" *Stem Cells*. 2004, 22:531-543.

Rosada et al. "The human umbilical cord blood: A potential source for osteoblast progenitor cells." *Calcified Tissue International*. 2003, 72:135-142.

Simonson et al. "Telomerase expression extends the proliferative life-span and maintains the osteogenic potential of human bone marrow stromal cells." *Nature Biotechnology*. 2002, 20: 592-596.

Terai et al. "Immortalization of human fetal cells: the life span of umbilical cord blood-derived cells can be prolonged without manipulating p16INK4a/RB braking pathway." *Molecular Biology of the Cell*. Mar. 2005, 16:1491-1499.

International Search Report and Written Opinion mailed Apr. 27, 2007 in PCT/US06/33129, 23 pages.

Supplementary Search Report mailed Nov. 28, 2007 in PCT/US2005013244, 50 pages.

International Search Report and Written Opinion mailed Dec. 12, 2006 in PCT/US05/13244, 58 pages.

Jones et al., "Isolation and Characterization of Bone Marrow Multipotential Mesenchymal Progenitor Cells," *Arth. Rheum.*, 2002, 46(12):3349-3360.

Kern et al., "Comparative Analysis of Mesenchymal Stem Cells from Bone Marrow, Umbilical Cord Blood, or Adipose Tissue," *Stem Cells*, 2006, 24:1294-1301.

Krause et al., "Multi-Organ, Multi-Lineage Engraftment by a Single Bone Marrow-Derived Stem Cell," *Cell*, 2001, 105:369-377.

Lee et al., "Isolation of multipotent mesenchymal stem cells from umbilical cord blood," *Blood*, 2004, 103(5):1669-1675.

Meng et al., "Endometrial regenerative cells: A novel stem cell population," *J. Translational Med.*, 2007, 5:57.

Phinney and Prockop, "Concise Review: Mesenchymal Stem/Multipotent Stromal Cells: The State of Transdifferentiation and Modes of Tissue Repair—Current Views," *Stem Cells*, 2007, 25:2896-2902.

Pittenger et al., "Adult mesenchymal stem cells: potential For muscle and tendon regeneration and use in gene therapy," *J. Musculoskel. Neuron. Interact.*, 2002, 2(4):309-320.

Sakaguchi et al., "Comparison of Human Stem Cells Derived From Various Mesenchymal Tissues," *Arth. Rheum.*, 2005, 52(8):2521-2529.

Stefano et al., "Endogenous morphine/nitric oxide-coupled regulation of cellular physiology and gene expression: Implications for cancer biology," *Semin. Cancer Biol.*, 2008, 18(3):199-210.

Wagner et al., "Comparative characteristics of mesenchymal stem cells from human bone marrow, adipose tissue, and umbilical cord blood," *Exp. Hematol.*, 2005, 33:1402-1416.

Office Action mailed Feb. 6, 2008 in U.S. Appl. No. 11/208,873, 20 pages.

Abe et al., "Cells Derived from the Circulation Contribute to the Repair of Lung Injury," *Am. J. Respir. Crit. Care Med.*, 2004, 170(11):1158-1163.

Baksh et al., "Adult mesenchymal stem cells: characterization, differentiation, and application in cell and gene therapy," *J. Cell. Mol. Med.*, 2004, 8(3):301-316.

Bensidhoum et al., "Homing of in vitro expanded Stro-1⁻ or Stro-1⁺ human mesenchymal stem cells into the NOD/SCID mouse and their role in supporting human CD34 cell engraftment," *Blood*, 2004, 103:3313-3319.

Bieback et al., "Critical Parameters for the Isolation of Mesenchymal Stem Cells from Umbilical Cord Blood," *Stem Cells*, 2004, 22:625-634.

Cadet et al., "A Functionally Coupled µ3-Like Opiate Receptor/Nitric Oxide Regulatory Pathway in Human Multi-Lineage Progenitor Cells," *J. Immunol.*, 2007, 179:5839-5844.

Choi et al., "Chondrogenic differentiation of human umbilical cord blood-derived multilineage progenitor cells in atelocollagen," *Cytotherapy*, 2008, 0:1-9.

D'Ippolito et al., "Marrow-isolated adult multilineage inducible (Miami) cells, a unique population of postnatal young and old human cells with extensive expansion and differentiation potential," *J. Cell. Sci.*, 2004, 117:2971-2981.

Erices et al., "Mesenchymal progenitor cells in human umbilical cord blood," *Br. J. Haematol.*, 2000, 109:235-242.

Jiang et al., "Pluripotency of mesenchymal stem cells derived from adult marrow," *Nature*, 2002, 418(6893):41-49.

BD™ Biosciences Technical Bulletin BD™ Three Dimensional Collagen Composite and OPLA Scaffolds, 2002.

Lechner et al., "Clonal growth of epithelial cells from normal adult human bronchus," *Cancer Res.*, 1981, 41:2294-2304.

Authorized Officer Michael A. Belyavski, International Search Report/Written Opinion, PCT/US05/13244, mailed Dec. 12, 2006, 7 pages.

Authorized Officer Yoshiko Kuwahara, International Preliminary Report on Patentability, PCT/US05/13244, mailed Jan. 11, 2007, 5 pages.

Supplementary European Search Report, EP Application No. 05 73 6785, mailed Nov. 28, 2007, 6 pages.

Examination Report, EP Application No. 05 73 6785, mailed Mar. 3, 2008, 6 pages.

The Patent Office of the State Intellectual Property Office of the People's Republic of China, Examination Report, Chinese Application No. 200580012739.3, mailed Mar. 9, 2009, 10 pages.

Examination Report, Australian Application No. 2005241008, mailed March 25, 2009, 5 pages.

Office Action, U.S. Appl. No. 11/452,502, mailed Jan. 14, 2009, 13 pages.

Authorized Officer Q. Janice Li, International Search Report/Written Opinion, PCT/US07/66797, mailed Sep. 23, 2008, 9 pages.

Authorized Officer Philippe Becamel, International Preliminary Report on Patentability, PCT/US07/66797, mailed Oct. 30, 2008, 6 pages.

Office Action, U.S. Appl. No. 11/736,273, mailed Apr. 28, 2009, 12 pages.

Authorized Officer Jung Hee Han, International Search Report/Written Opinion, PCT/US2008/71207, mailed Feb. 11, 2009, 10 pages.

Communication Pursuant to Article 94(3) EPC, EP Application No. 05 736 785 mailed Jul. 22, 2009, 4 pages.

Lechner et al., "Clonal growth of epithelial cells from normal adult human bronchus," *Cancer Res.*, 1981, 41:2294-2304.

* cited by examiner

FIG 2
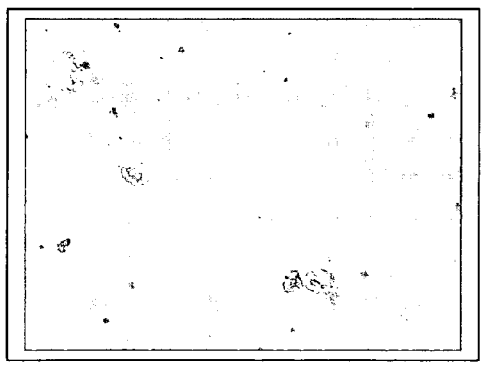
FIG 2A
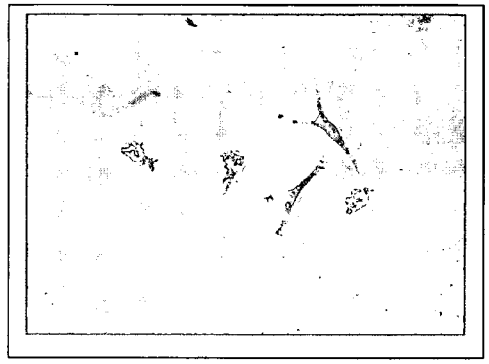
FIG 2B
FIG 2C
FIG 2D

MULTI-LINEAGE PROGENITOR CELLS

CROSS-REFERENCE TO RELATED APPLICATION

This application claims priority from U.S. Provisional Application Ser. No. 60/564,687, filed on Apr. 23, 2004.

TECHNICAL FIELD

The invention relates to multi-lineage progenitor cells (MLPC) from human blood and more particularly, to MLPC with the potential to differentiate into multiple tissue lineages and use of such cells for regenerative therapies.

BACKGROUND

Progenitor cells capable of hematopoietic reconstitution after myeloablative therapy have been identified in a number of sources including the bone marrow, umbilical cord and placental blood, and in the peripheral blood of subjects treated with stem cell-mobilizing doses of granulocyte-colony stimulation factor. These cells, often referred to as hematopoietic stem cells (HSC), are identified by the presence of cell surface glycoproteins such as CD34 and CD133. HSC represent a very small percentage of the total population of cells given as part of a 'bone marrow transplant' and are considered to be the life-saving therapeutic portion of this treatment responsible for the restoration of the blood-forming capacity of patients given myeloablative doses of chemotherapy or radiation therapy. Stem cell therapies via bone marrow transplantation have become a standard treatment for a number of intractable leukemias and genetic blood disorders.

Recent studies have suggested the presence of a more primitive cell population in the bone marrow capable of self-renewal as well as differentiation into a number of different tissue types other than blood cells. These multi-potential cells were discovered as a minor component in the CD34-plastic-adherent cell population of adult bone marrow, and are variously referred to as mesenchymal stem cells (MSC) (Pittenger, et al., *Science* 284:143-147 (1999)) or multi-potent adult progenitor cells (MAPC) cells (Furcht, L. T., et al., U.S. patent publication 20040107453 A1). MSC cells do not have a single specific identifying marker, but have been shown to be positive for a number of markers, including CD29, CD90, CD105, and CD73, and negative for other markers, including CD14, CD3, and CD34. Various groups have reported to differentiate MSC cells into myocytes, neurons, pancreatic beta-cells, liver cells, bone cells, and connective tissue. Another group (Wernet et al., U.S. patent publication 20020164794 A1) has described an unrestricted somatic stem cell (USSC) with multi-potential capacity that is derived from a CD45/CD34 population within cord blood.

SUMMARY

The invention is based on the identification of a rare undifferentiated cell population from human fetal blood that is capable of self-renewal and has the potential to differentiate into cells representing each of the three embryonic germ layers. These fetal blood-derived cells are referred to as multi-lineage progenitor cells (MLPC). As described herein, fetal blood MLPC are distinguished from bone marrow-derived MSC, HSC, and USSC on the basis of their immunophenotypic characteristics, morphology, and distinct growth pattern. The invention provides methods for developing monotypic clonal cell lines from individual cells. The invention also provides methods for cryopreserving MLPC (e.g., for cord blood banking) and methods of using MLPC in regenerative therapies.

In one aspect, the invention features a purified population of human fetal blood (e.g., cord blood) MLPC, wherein the MLPC are positive for CD9 and CD45. The MLPC can display a leukocyte morphology. The MLPC can be further positive for SSEA-4 or CD34, as well as CD133, CD41, CD44, CD105, CD29, CD73, CD90, stem cell factor, SSEA-3, and CD13. The MLPC can be negative for CD15, CD38, glycophorin-A, CD2, CD3, CD8, CD19, CD20, CD22, CD5, CD7, CD10, CD14, CD4, HLA-DR, CD16, CD33, and CD61. The MLPC can attain a fibroblast-like morphology over time in culture. The MLPC also can adhere to a plastic surface when cultured. The MLPC are capable of differentiating into cells from all three embryonic germ layers, including, for example, cells having an osteocytic phenotype, cells having an adipocytic phenotype, cells having a neural stem cell phenotype, cells having a myocytic phenotype, cells having an endothelial phenotype, cells having a hepatocytic, phenotype, and cells having a pancreatic phenotype. The MLPC can include an exogenous nucleic acid (e.g., an exogenous nucleic acid encoding a polypeptide).

In another aspect, the invention features a purified population of human fetal blood (e.g., cord blood) MLPC, wherein the MLPC are positive for CD9, negative for CD45, negative for CD34, and negative for SSEA-4. The MLPC can display a fibroblast morphology. The MLPC can be further positive for CD13, CD29, CD44, CD73, CD90, and CD105, and can be further negative for CD2, CD3, CD4, CD5, CD7, CD8, CD10, CD14, CD15, CD16, CD19, CD20, CD22, CD33, CD36, CD38, CD41, CD61, CD62E, CD133, glycophorin-A, stem cell factor, SSEA-3, and HLA-DR. The MLPC can adhere to a plastic surface when cultured. The MLPC are capable of differentiating into cells from all three embryonic germ layers, including, for example, cells having an osteocytic phenotype, cells having an adipocytic phenotype, cells having a neural stem cell phenotype, cells having a myocytic phenotype, cells having an endothelial phenotype, cells having a hepatocytic phenotype, and cells having a pancreatic phenotype. The MLPC can include an exogenous nucleic acid (e.g., an exogenous nucleic acid encoding a polypeptide).

The invention also features a clonal line of human fetal blood (e.g., cord blood) MLPC, wherein the MLPC are positive for CD9, negative for CD45, negative for CD34, and negative for SSEA-4. The MLPC can display a fibroblast morphology. The MLPC can be further positive for CD13, CD29, CD44, CD73, CD90, and CD105, and can be further negative for CD2, CD3, CD4, CD5, CD7, CD8, CD10, CD14, CD15, CD16, CD19, CD20, CD22, CD33, CD36, CD38, CD41, CD61, CD62E, CD133, glycophorin-A, stem cell factor, SSEA-3, and HLA-DR. The MLPC can adhere to a plastic surface when cultured. The MLPC are capable of differentiating into cells from all three embryonic germ layers, including, for example, cells having an osteocytic phenotype, cells having an adipocytic phenotype, cells having a neural stem cell phenotype, cells having a myocytic phenotype, cells having an endothelial phenotype, cells having a hepatocytic phenotype, and cells having a pancreatic phenotype. The MLPC can include an exogenous nucleic acid (e.g., an exogenous nucleic acid encoding a polypeptide). In some embodiments, the MLPC have undergone at least 5 doublings (e.g., at least 8, at least 10, at least 15, or at least 25 doublings) in culture.

In another aspect, the invention features a composition that includes a purified population of MLPC or a clonal line of MLPC and a culture medium. The composition further can include a cryopreservative. In one embodiment, the cryopreservative is dimethylsulfoxide (DMSO) (e.g., 1 to 10% DMSO). In another embodiment, the cryopreservative is fetal bovine serum, human serum, or human serum albumin in combination with one or more of the following: DMSO, trehalose, and dextran. For example, the cryopreservative can be DMSO and trehalose, or fetal bovine serum and DMSO.

In yet an another aspect, the invention features an article of manufacture that includes a purified population of MLPC or a clonal line of MLPC. The purified population of MLPC or the clonal line can be housed within a container (e.g., a vial or a bag). The container further can include a cryopreservative.

The invention also features a method for purifying a population of MLPC from human fetal blood. The method includes contacting a human fetal blood sample (e.g., cord blood) with a composition that includes dextran, anti-glycophorin A antibody, anti-CD15 antibody, and anti-CD9 antibody; allowing the sample to partition into an agglutinate and a supernatant phase; recovering cells from the supernatant phase; and purifying MLPC from the recovered cells by adherence to a solid substrate (e.g., a plastic substrate), wherein the MLPC are positive for CD9 and positive for CD45. The MLPC can be further positive for CD34, CD133, CD41, CD44, CD105, CD29, CD73, CD90, stem cell factor, SSEA-3, SSEA-4, and CD13. The MLPC can be further negative for CD15, CD38, glycophorin-A, CD2, CD3, CD8, CD19, CD20, CD22, CD5, CD7, CD10, CD14, CD4, HLA-DR, CD16, CD33, and CD61. The method further can include testing the MLPC for CD9 or testing for CD9, CD29, CD45, CD73, and CD90.

The method further can include culturing the MLPC such that the MLPC obtain a fibroblast morphology, wherein the MLPC, after obtaining the fibroblast morphology, are positive for CD9, negative for CD45, negative for CD34, and negative for SSEA-4. The MLPC, after obtaining the fibroblast morphology, can be further positive for CD13, CD29, CD44, CD73, CD90, and CD105. The MLPC, after obtaining the fibroblast morphology, can be further negative for CD2, CD3, CD4, CD5, CD7, CD8, CD10, CD14, CD15, CD16, CD19, CD20, CD22, CD33, CD36, CD38, CD41, CD61, CD62E, CD133, glycophorin-A, stem cell factor, SSEA-3, and HLA-DR. The method further can include testing the MLPC for CD9 or testing for CD9, CD29, CD45, CD73, and CD90.

In another aspect, the invention features a method for cryopreserving MLPC. The method includes contacting a purified population of MLPC or clonal line of MLPC with a cryopreservative; and freezing the purified population of MLPC or the clonal line. In one embodiment, the cryopreservative is DMSO (e.g., 1 to 10% DMSO). In another embodiment, the cryopreservative is fetal bovine serum, human serum, or human serum albumin in combination with one or more of the following: DMSO, trehalose, and dextran. For example, the cryopreservative can be DMSO and trehalose, or fetal bovine serum and DMSO. The purified population of MLPC or the clonal line can be suspended in the cryopreservative at a concentration between $1 \times 10^5$ and $5 \times 10^7$ cells/mL. The purified population or clonal line can be frozen at a controlled rate (e.g., the freezing rate is controlled electronically) or by placement in an ethanol bath in the vapor phase of a liquid nitrogen cryogenic storage tank.

In yet another aspect, the invention features a method of producing a population of differentiated cells. The method includes culturing a purified population of MLPC or a clonal line of MLPC with an agent effective to induce differentiation of the MLPC. The agent can include insulin, glutamine, dexamethasone, indomethacin, and 3-isobutyl-1-methyl-xanthine; dexamethasone, glutamine, ascorbate, and β-glycerophosphate; epithelial growth factor, insulin, fetuin, dexamethasone, and fibroblast growth factor-basic; fibroblast growth factor-basic, epidermal growth factor, NSF-1, and retinoic acid; heparin, bovine brain extract, epithelial growth factor; and hydrocortisone; or ascorbic acid, hydrocortisone, transferrin, insulin, epidermal growth factor, hepatocyte growth factor, fibroblast growth factor-basic, fibroblast growth factor-4, and stem cell factor.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 2A-2D are photomicrographs depicting the morphology of developing MLPC. FIG. 2A shows an early culture of MLPC isolated from umbilical cord blood demonstrating the cells in the leukocyte morphology phase. FIG. 2B shows a culture of MLPC beginning to change their morphology from leukocyte to fibroblast morphology. FIG. 2C shows a later culture of MLPC in logarithmic growth phase. FIG. 2D shows a fully confluent culture of MLPC.

DETAILED DESCRIPTION

Figure 1:
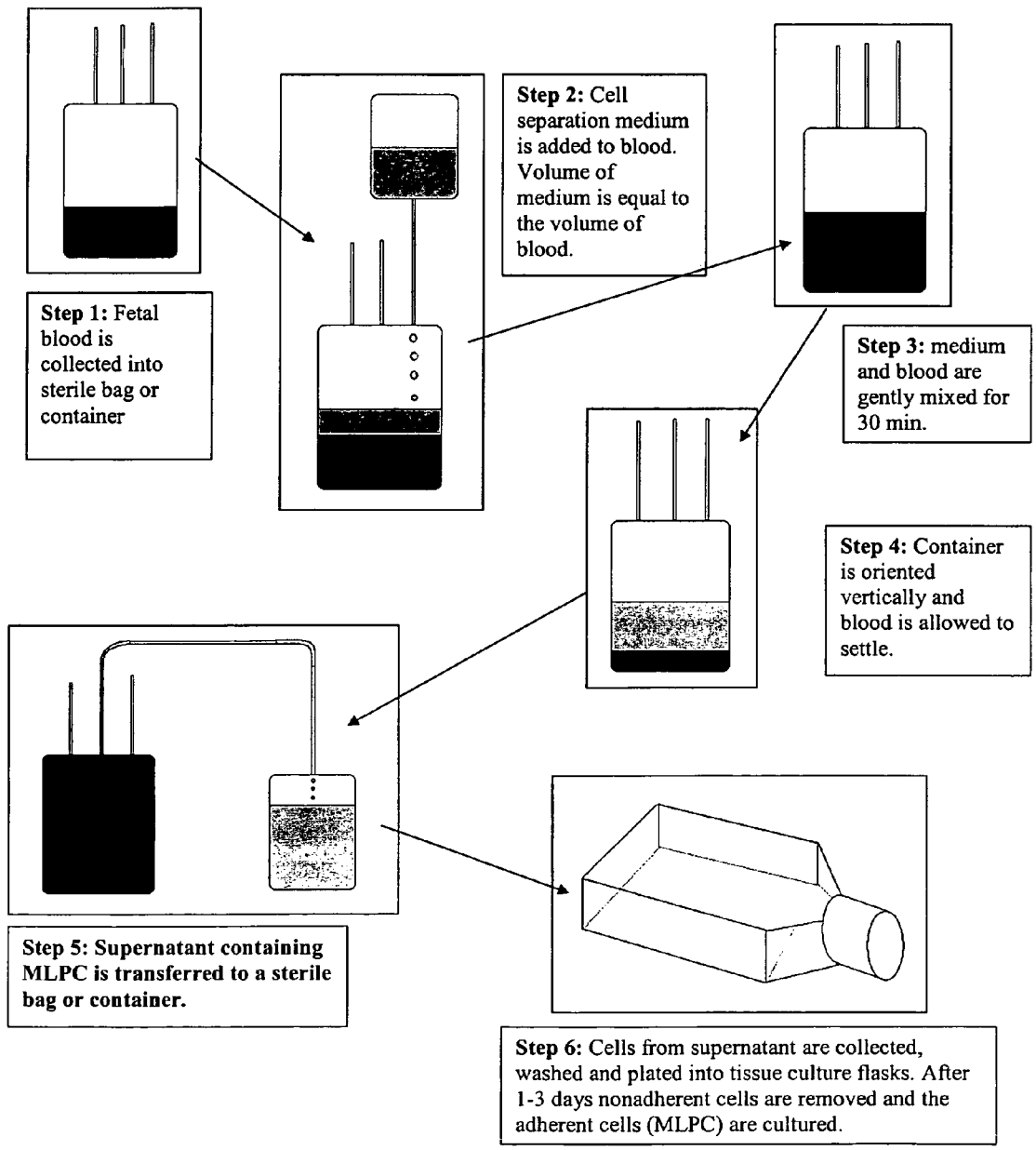
FIG. 1 is a schematic of a cell separation procedure for purifying MLPC from fetal blood.

In general, the invention provides purified populations of MLPC from human fetal blood (e.g., umbilical cord blood ("cord blood"), placental blood, or the blood from a fetus) and clonal MLPC lines derived from individual MLPC. Fetal blood provides a source of cells that is more immature than adult bone marrow and has a higher percentage of cells bearing immature cell surface markers. Consequently, there may be advantages in the expansion and differentiation capacity of the progenitor cells from fetal blood. As described herein, MLPC have immunophenotypic characteristics distinct from bone marrow derived MSC's, bone marrow-derived HSC, and umbilical cord blood-derived HSC and USSC. The cells described herein have the capacity to self renew and differentiate into diverse tissue types similar to the bone marrow-derived MSC and MAPC cells. MLPC can be used to develop cellular therapies and establish cryopreserved cell banks for future regenerative medicine procedures. MLPC also can be modified such that the cells can produce one or more polypeptides or other therapeutic compounds of interest.

Cell Separation Compositions

MLPC can be isolated from fetal blood (e.g., cord blood) using the negative selection process and cell separation compositions disclosed in U.S. patent Publication No. 2003-0027233-A1. Such cell compositions can include dextran and one or more antibodies against (i.e., that have binding affinity for) a cell surface antigen.

Dextran is a polysaccharide consisting of glucose units linked predominantly in alpha (1 to 6) mode. Dextran can cause stacking of erythrocytes (i.e., rouleau formation) and thereby facilitate the removal of erythroid cells from solution. Antibodies against cell surface antigens can facilitate the removal of blood cells from solution via homotypic agglutination (i.e., agglutination of cells of the same cell type) and/or heterotypic agglutination (i.e., agglutination of cells of different cell types).

For example, a cell separation composition can include dextran and antibodies against glycophorin A, CD15, and CD9. Cell separation compositions also can contain antibodies against other blood cell surface antigens including, for example, CD2, CD3, CD4, CD8, CD72, CD16, CD41a, HLA Class I, HLA-DR, CD29, CD11a, CD11b, CD11c, CD19, CD20, CD23, CD39, CD40, CD43, CD44, CDw49d, CD53, CD54, CD62L, CD63, CD66, CD67, CD81, CD82, CD99, CD100, Leu-13, TPA-1, surface Ig, and combinations thereof. Thus, cell separation compositions can be formulated to selectively agglutinate particular types of blood cells.

Typically, the concentration of anti-glycophorin A antibodies in a cell separation composition ranges from 0.1 to 15 mg/L (e.g., 0.1 to 10 mg/L, 1 to 5 mg/L, or 1 mg/L). Anti-glycophorin A antibodies can facilitate the removal of red cells from solution by at least two mechanisms. First, anti-glycophorin A antibodies can cause homotypic agglutination of erythrocytes since glycophorin A is the major surface glycoprotein on erythrocytes. In addition, anti-glycophorin A antibodies also can stabilize dextran-mediated rouleau formation. Exemplary monoclonal anti-glycophorin A antibodies include, without limitation, 107FMN (Murine IgG1 isotype), YTH89.1 (Rat IgG2b isotype), 2.2.2.E7 (Murine IgM isotype; BioE, St. Paul, Minn.), and E4 (Murine IgM isotype). See e.g., M. Vanderlaan et al., *Molecular Immunology* 20:1353 (1983); Telen M. J. and Bolk, T. A., *Transfusion* 27:309 (1987); and Outram S. et al., *Leukocyte Research*. 12:651 (1988).

The concentration of anti-CD15 antibodies in a cell separation composition can range from 0.1 to 15 mg/L (e.g., 0.1 to 10, 1 to 5, or 1 mg/L). Anti-CD15 antibodies can cause homotypic agglutination of granulocytes by crosslinking CD15 molecules that are present on the surface of granulocytes. Anti CD15 antibodies also can cause homotypic and heterotypic agglutination of granulocytes with monocytes, NK-cells and B-cells by stimulating expression of adhesion molecules (e.g., L-selectin and beta-2 integrin) on the surface of granulocytes that interact with adhesion molecules on monocytes, NK-cells and B-cells. Heterotypic agglutination of these cell types can facilitate the removal of these cells from solution along with red cell components. Exemplary monoclonal anti-CD15 antibodies include, without limitation, AHN1.1 (Murine IgM isotype), FMC-10 (Murine IgM isotype), BU-28 (Murine IgM isotype), MEM-157 (Murine IgM isotype), MEM-158 (Murine IgM isotype), 324.3.B9 (Murine IgM isotype; BioE, St. Paul, Minn.), and MEM-167 (Murine IgM isotype). See e.g., *Leukocyte typing IV* (1989); *Leukocyte typing II* (1984); *Leukocyte typing VI* (1995); Solter D. et al., *Proc. Natl. Acad. Sci. USA* 75:5565 (1978); Kannagi R. et al., *J. Biol. Chem.* 257:14865 (1982); Magnani, J. L. et al., *Arch. Biochem. Biophys* 233:501 (1984); Eggens I. et al., *J. Biol. Chem.* 264:9476 (1989).

The concentration of anti-CD9 antibodies in a cell separation composition can range from 0.1 to 15, 0.1 to 10, 1 to 5, or 1 mg/L. Anti-CD9 antibodies can cause homotypic agglutination of platelets. Anti-CD9 antibodies also can cause heterotypic agglutination of granulocytes and monocytes via platelets that have adhered to the surface of granulocytes and monocytes. CD9 antibodies can promote the expression of platelet p-selectin (CD62P), CD41/61, CD31, and CD36, which facilitates the binding of platelets to leukocyte cell surfaces. Thus, anti-CD9 antibodies can promote multiple cell-cell linkages and thereby facilitate agglutination and removal from solution. Exemplary monoclonal anti-CD9 antibodies include, without limitation, MEM-61 (Murine IgG1 isotype), MEM-62 (Murine IgG1 isotype), MEM-192 (Murine IgM isotype), FMC-8 (Murine IgG2a isotype), SN4 (Murine IgG1 isotype), 8.10.E7 (Murine IgM isotype; BioE, St. Paul, Minn.), and BU-16 (Murine IgG2a isotype). See e.g., *Leukocyte typing VI* (1995); *Leukocyte typing II* (1984); Von dem Boume A. E. G. Kr. and Moderman P. N. (1989) In *Leukocyite typing IV* (ed. W. Knapp, et al), pp. 989-92, Oxford University Press, Oxford; Jennings, L. K., et al. In *Leukocyte typing V*, ed. S. F. Schlossmann et al., pp. 1249-51, Oxford University Press, Oxford (1995); Lanza F. et al., *J. Biol. Chem.* 266:10638 (1991); Wright et al., *Immunology Today* 15:588 (1994); Rubinstein E. et al., *Seminars in Thrombosis and Hemostasis* 21:10 (1995).

In some embodiments, a cell separation composition contains antibodies against CD41, which can selectively agglutinate platelets. In some embodiments, a cell separation composition contains antibodies against CD3, which can selectively agglutinate T-cells. In some embodiments, a cell separation composition contains antibodies against CD2, which can selectively agglutinate T-cells and NK cells. In some embodiments, a cell separation composition contains antibodies against CD72, which can selectively agglutinate B-cells. In some embodiments, a cell separation composition contains antibodies against CD16, which can selectively agglutinate NK cells and neutrophilic granulocytes. The concentration of each of these antibodies can range from 0.01 to 15 mg/L. Exemplary anti-CD41 antibodies include, without limitation, PLT-1 (Murine IgM isotype), CN19 (Murine $IgG_1$ isotype), and 8.7.C3 (Murine IgG1 isotype). Non-limiting examples of anti-CD3 antibodies include OKT3 (Murine $IgG_1$), HIT3a (Murine IgG2a isotype), SK7 (Murine $IgG_1$) and BC3 (Murine $IgG_{2a}$). Non-limiting examples of anti-CD2 antibodies include 7A9 (Murine IgM isotype), T11 (Murine $IgG_1$ isotype), and Leu5b (Murine $IgG_{2a}$ Isotype). Non-limiting examples of anti-CD72 antibodies include BU-40 (Murine $IgG_1$ isotype) and BU-41 (Murine $IgG_1$ isotype). Non-limiting examples of anti-CD16 antibodies include 3G8 (Murine IgG).

As mentioned above, cell separation compositions can be formulated to selectively agglutinate particular blood cells. As an example, a cell separation composition containing antibodies against glycophorin A, CD15, and CD9 can facilitate the agglutination of erythrocytes, granulocytes, NK cells, B cells, and platelets. T cells, NK cells and rare precursor cells such as MLPC then can be recovered from solution. If the formulation also contained an antibody against CD3, T cells also could be agglutinated, and NK cells and rare precursors such as MLPC could be recovered from solution.

Cell separation compositions can contain antibodies against surface antigens of other types of cells (e.g., cell surface proteins of tumor cells). Those of skill in the art can use routine methods to prepare antibodies against cell surface antigens of blood, and other, cells from humans and other mammals, including, for example, non-human primates, rodents (e.g., mice, rats, hamsters, rabbits and guinea pigs), swine, bovines, and equines.

Typically, antibodies used in the composition are monoclonal antibodies, which are homogeneous populations of antibodies to a particular epitope contained within an antigen. Suitable monoclonal antibodies are commercially available, or can be prepared using standard hybridoma technology. In particular, monoclonal antibodies can be obtained by techniques that provide for the production of antibody molecules by continuous cell lines in culture, including the technique described by Kohler, G. et al., *Nature*, 1975, 256:495, the human B-cell hybridoma technique (Kosbor et al., *Immunology Today* 4:72 (1983); Cole et al., *Proc. Natl. Acad. Sci. USA* 80:2026 (1983)), and the EBV-hybridoma technique (Cole et al., "Monoclonal Antibodies and Cancer Therapy," Alan R. Liss, Inc., pp. 77-96 (1983)).

Antibodies can be of any immunoglobulin class including IgG, IgM, IgE, IgA, IgD, and any subclass thereof. Antibodies of the IgG and IgM isotypes are particularly useful in cell separation compositions of the invention. Pentameric IgM antibodies contain more antigen binding sites than IgG antibodies and can, in some cases (e.g., anti-glycophorin A and anti-CD15), be particularly useful for cell separation reagents. In other cases (e.g., anti-CD9 antibodies), antibodies of the IgG isotype are particularly useful for stimulating homotypic and/or heterotypic agglutination.

Antibodies against cell surface antigens can be provided in liquid phase (i.e., soluble). Liquid phase antibodies typically are provided in a cell separation composition at a concentration between about 0.1 and about 15 mg/l (e.g., between 0.25 to 10, 0.25 to 1, 0.5 to 2, 1 to 2, 4 to 8, 5 to 10 mg/l).

Antibodies against cell surface antigens also can be provided in association with a solid phase (i.e., substrate-bound). Antibodies against different cell surface antigens can be covalently linked to a solid phase to promote crosslinking of cell surface molecules and activation of cell surface adhesion molecules. The use of substrate-bound antibodies can facilitate cell separation (e.g., by virtue of the mass that the particles contribute to agglutinated cells, or by virtue of properties useful for purification).

In some embodiments, the solid phase with which a substrate-bound antibody is associated is particulate. In some embodiments, an antibody is bound to a latex microparticle such as a paramagnetic bead (e.g., via biotin-avidin linkage, covalent linkage to COO groups on polystyrene beads, or covalent linkage to $NH_2$ groups on modified beads). In some embodiments, an antibody is bound to an acid-etched glass particle (e.g., via biotin-avidin linkage). In some embodiments, an antibody is bound to an aggregated polypeptide such as aggregated bovine serum albumin (e.g., via biotin-avidin linkage, or covalent linkage to polypeptide COO groups or $NH_2$ groups). In some embodiments, an antibody is covalently linked to a polysaccharide such as high molecular weight (e.g., >1,000,000 $M_r$) dextran sulfate. In some embodiments, biotinylated antibodies are linked to avidin particles, creating tetrameric complexes having four antibody molecules per avidin molecule. In some embodiments, antibodies are bound to biotinylated agarose gel particles (One Cell Systems, Cambridge, Mass., U.S.A.) via biotin-avidin-biotinylated antibody linkages. Such particles typically are about 300-500 microns in size, and can be created in a sonicating water bath or in a rapidly mixed water bath.

Cell-substrate particles (i.e., particles including cells and substrate-bound antibodies) can sediment from solution as an agglutinate. Cell-substrate particles also can be removed from solution by, for example, an applied magnetic field, as when the particle is a paramagnetic bead. Substrate-bound antibodies typically are provided in a cell separation composition at a concentration between about 0.1 and about $50.0 \times 10^9$ particles/l (e.g., between 0.25 to $10.0 \times 10^9$, 1 to $20.0 \times 10^9$, 2 to $10.0 \times 10^9$, 0.5 to $2 \times 10^9$, 2 to $5 \times 10^9$, 5 to $10 \times 10^9$, and 10 to $30 \times 10^9$ particles/l), where particles refers to solid phase particles having antibodies bound thereto.

Cell separation compositions also can contain divalent cations (e.g., $Ca^{+2}$ and $Mg^{+2}$). Divalent cations can be provided, for example, by a balanced salt solution (e.g., Hank's balanced salt solution). $Ca^{+2}$ ions reportedly are important for selectin-mediated and integrin-mediated cell-cell adherence.

Cell separation compositions also can contain an anticoagulant such as heparin. Heparin can prevent clotting and non-specific cell loss associated with clotting in a high calcium environment. Heparin also promotes platelet clumping. Clumped platelets can adhere to granulocytes and monocytes and thereby enhance heterotypic agglutination more so than single platelets. Heparin can be supplied as a heparin salt (e.g., sodium heparin, lithium heparin, or potassium heparin).

Populations and Clonal Lines of MLPC

MLPC can be purified from human fetal blood using a cell separation composition described above. As used herein, "purified" means that at least 90% (e.g., 91, 92, 93, 94, 95, 96, 97, 98, or 99%) of the cells within the population are MLPC. As used herein, "MLPC" refers to fetal blood cells that are positive for CD9 and typically display a constellation of other markers such as CD13, CD73, and CD105. "MLPC population" refers to the primary culture obtained from the human fetal blood and uncloned progeny thereof. "Clonal line" refers to a cell line derived from a single cell. As used herein, a "cell line" is a population of cells able to renew themselves for extended periods of times in vitro under appropriate culture conditions. The term "line," however, does not indicate that the cells can be propagated indefinitely. Rather, clonal lines described herein typically can undergo 75 to 100 doublings before senescing.

Typically, an MLPC population is obtained by contacting a fetal blood sample with a cell separation composition described above and allowing the sample to partition into an agglutinate and a supernatant phase. For example, the sample can be allowed to settle by gravity or by centrifugation. Preferably, MLPC are purified from an umbilical cord blood sample that is less than 48 hours old (e.g., less than 24, 12, 8, or 4 hours post-partum). After agglutination, unagglutinated cells can be recovered from the supernatant phase. For example, cells in the supernatant phase can be recovered by centrifugation then washed with a saline solution and plated on a solid substrate (e.g., a plastic culture device such as a chambered slide or culture flask), using a standard growth medium with 10% serum (e.g., DMEM with 10% serum; RPMI-1640 with 10% serum, or mesenchymal stem cell growth medium with 10% serum (catalog # PT-3001, Cambrex, Walkersville, Md.). MLPC attach to the surface of the solid substrate while other cells, including T cells, NK cells and CD34+ HSC, do not and can be removed with washing. The MLPC change from the leukocyte morphology to the fibrobiastic morphology between 3 days and 2 weeks post initiation of culture after which the cells enter logarithmic growth phase and will continue growing logarithmically as long as cultures are maintained at cell concentrations of less than about $1.5 \times 10^5$ cells/cm$^2$.

Clonal lines can be established by harvesting the MLPC then diluting and re-plating the cells on a multi-well culture plate such that a single cell can be found in a well. Cells can be transferred to a larger culture flask after a concentration of 1 to $5 \times 10^5$ cells/75 cm$^2$ is reached. Cells can be maintained at a concentration between $1 \times 10^5$ and $5 \times 10^5$ cells/75 cm$^2$ for logarithmic growth.

MLPC can be assessed for viability, proliferation potential, and longevity using techniques known in the art. For example, viability can be assessed using trypan blue exclusion assays, fluorescein diacetate uptake assays, or propidium iodide uptake assays. Proliferation can be assessed using thymidine uptake assays or MTT cell proliferation assays. Longevity can be assessed by determining the maximum number of population doublings of an extended culture.

MLPC can be immunophenotypically characterized using known techniques. For example, the cell culture medium can be removed from the tissue culture device and the adherent cells washed with a balanced salt solution (e.g., Hank's balanced salt solution) and bovine serum albumin (e.g., 2% BSA). Cells can be incubated with an antibody having binding affinity for a cell surface antigen such as CD9, CD45, CD13, C73, CD105, or any other cell surface antigen. The antibody can be detectably labeled (e.g., fluorescently or enzymatically) or can be detected using a secondary antibody that is detectably labeled. Alternatively, the cell surface antigens on MLPC can be characterized using flow cytometry and fluorescently labeled antibodies.

As described herein, the cell surface antigens present on MLPC can vary, depending on the stage of culture. Early in culture when MLPC display a leukocyte-like morphology, MLPC are positive for CD9 and CD45, SSEA-4 (stage-specific embryonic antigen-4), CD34, as well as CD13, CD29, CD41, CD44, CD73, CD90, CD105, stem cell factor, STRO-1 (a cell surface antigen expressed by bone marrow stromal cells), SSEA-3 (galactosylgloboside), and CD133, and are negative for CD15, CD38, glycophorin A (CD235a), and lineage markers CD2, CD3, CD4, CD5, CD7, CD8, CD10, CD11b, CD16, CD19, CD20, CD21, CD22, CD33, CD36, CD41, CD61, CD62E, CD72, HLA-DR, and CD102. After transition to the fibroblastic morphology, MLPC remain positive for CD9, CD13, CD29, CD73, CD90, and CD105, and become negative for CD34, CD41, CD45, stem cell factor, STRO-1, SSEA-3, SSEA-4, and CD133. At all times during in vitro culture, the undifferentiated MLPC are negative for CD15, CD38, glycophorin A (CD235a), lineage markers CD2, CD3, CD4, CD5, CD7, CD8, CD10, CD11b, CD16, CD19, CD20, CD21, CD22, CD33, CD36, CD41, CD61, CD62E, CD72, HLA-DR, and CD102.

Bone marrow-derived MSC and MAPC as well as the cord blood-derived USSC have been described as being derived from a CD45$^-$/CD34$^-$ cell population. MLPC are distinguished from those cell types as being a CD45$^+$/CD34$^+$ derived cell. Additionally, the presence and persistence of CD9 on the fetal blood-derived MLPC at all stages of maturation further distinguishes MLPC from MSC and MAPC, which do not possess CD9 as a marker. MLPC, which share the hematopoietic markers CD45, CD133, CD90 and CD34 during their leukocyte morphology phase, can be distinguished from HSC by their obligate plastic adherence and the presence of mesenchymal associated markers CD105, CD29, CD73, CD13 and embryonic associated markers SSEA-3 and SSEA-4. Additionally using currently available technology, HSC are unable to be cultured in vitro without further differentiation while MLPC can be expanded for many generations without differentiation. MLPC also differ from MSC and USSC by their more gracile in vitro culture appearance, thread-like cytoplasmic projections and their preference for low density culture conditions for optimal growth.

MLPC can be cryopreserved by suspending the cells (e.g. $5 \times 10^6$ to $2 \times 10^7$ cells/mL) in a cryopreservative such as dimethylsulfoxide (DMSO, typically 1 to 10%) or in fetal bovine serum, human serum, or human serum albumin in combination with one or more of DMSO, trehalose, and dextran. For example, (1) fetal bovine serum containing 10% DMSO; (2) human serum containing 10% DMSO and 1% Dextran; (3) human serum containing 1% DMSO and 5% trehalose; or (4) 20% human serum albumin, 1% DMSO, and 5% trehalose can be used to cryopreserve MLPC. After adding cryopreservative, the cells can be frozen (e.g., to −90° C.). In some embodiments, the cells are frozen at a controlled rate (e.g., controlled electronically or by suspending the cells in a bath of 70% ethanol and placed in the vapor phase of a liquid nitrogen storage tank. When the cells are chilled to −90° C., they can be placed in the liquid phase of the liquid nitrogen storage tank for long term storage. Cryopreservation can allow for long-term storage of these cells for therapeutic use.

Differentiation of MLPC

MLPC are capable of differentiating into a variety of cells, including cells of each of the three embryonic germ layers (i.e., endoderm, ectoderm, and mesoderm). As used herein, "capable of differentiating" means that a given cell, or its progeny, can proceed to a differentiated phenotype under the appropriate culture conditions. For example, MLPC can differentiate into cells having an osteocytic phenotype, cells having an adipocytic phenotype, cells having a neurocytic phenotype, cells having a myocytic phenotype, cells having an endothelial phenotype, cells having a hepatocytic/pancreatic precursor phenotype (also known as an oval cell) as well as other cell types. Differentiation can be induced using one or more differentiation agents, including without limitation, $Ca^{2+}$, an epidermal growth factor (EGF), a platelet derived growth factor (PDGF), a keratinocyte growth factor (KGF), a transforming growth factor (TGF), cytokines such as an interleukin, an interferon, or tumor necrosis factor, retinoic acid, transferrin, hormones (e.g., androgen, estrogen, insulin, prolactin, triiodothyronine, hydrocortisone, or dexamethasone), sodium butyrate, TPA, DMSO, NMF (N-methyl formamide), DMF (dimethylformamide), or matrix elements such as collagen, laminin, heparan sulfate).

Determination that an MLPC has differentiated into a particular cell type can be assessed using known methods, including, measuring changes in morphology and cell surface markers (e.g., by flow cytometry or immunohistochemistry), examining morphology by light or confocal microscopy, or by measuring changes in gene expression using techniques such as polymerase chain reaction (PCR) or gene-expression profiling.

For example, MLPC can be induced to differentiate into cells having an osteocytic phenotype using an induction medium (e.g., Osteogenic Differentiation Medium, catalog # PT-3002, from Cambrex) containing dexamethasone, L-glutamine, ascorbate, and β-glycerophosphate (Jaiswal et al., *J. Biol. Chem.* 64(2):295-312 (1997)). Cells having an osteocytic phenotype contain deposits of calcium crystals, which can be visualized, for example, using Alizarin red stain.

MLPC can be induced to differentiate into cells having an adipocytic phenotype using an induction medium (e.g., Adipogenic Differentiation Medium, catalog # PT-3004, from Cambrex) containing insulin, L-glutamine, dexamethasone, indomethacin, and 3-isobutyl-1-methyl-xanthine. Cells having an adipocytic phenotype contain lipid filled liposomes that can be visualized with Oil Red stain. Such cells also contain trigycerides, which fluoresce green with Nile Red stain (Fowler and Greenspan, *Histochem. Cytochem.* 33:833-836 (1985)).

MLPC can be induced to differentiate into cells having a myocytic phenotype using an induction medium (e.g., SkGM™, catalog # CC-3160, from Cambrex) containing EGF, insulin, Fetuin, dexamethasone, and FGF-basic (Wernet, et al., U.S. patent publication 20020164794 A1). Cells having a myocytic phenotype express fast skeletal muscle myosin and alpha actinin.

MLPC can be induced to differentiate into cells having a neural stem cell phenotype (neurospheres) using an induction medium (e.g., NPMM™—Neural Progenitor Maintenance medium, catalog #CC-3209, from Cambrex) containing human FGF-basic, human EGF, NSF-1, and FGF-4 and a culture device pre-coated with poly-D-lysine and laminin (e.g., from BD Biosciences Discovery Labware, catalog #354688). Once cells have been differentiated into neurospheres, they can be further differentiated into motor neurons with the addition of brain-derived neurotrophic factor (BDNF) and neurotrophin-3 (NT-3), astrocytes with the addition of leukemia inhibitory factor (LIF), retinoic acid and ciliary neurotrophic factor, and oligodendrocytes with the addition of 3,3', 5-triiodo-L-thyronine (T3). Neurocytic differentiation can be confirmed by the expression of nestin, class III beta-tubulin (tubulin β-4), glial fibrillary acidic protein (GFAP), and galactocerebroside (GalC). Neurospheres are positive for all such markers while some differentiated cell types are not. Differentiation into oligodendrocytes can be confirmed by positive staining for myelin basic protein (MBP).

MLPC can be induced to differentiate into cells having an endothelial phenotype using an endothelial growth medium (e.g., EGM™-MV, catalog # CC-3125, from Cambrex) containing heparin, bovine brain extract, epithelial growth factor (e.g., human recombinant epithelial growth factor), and hydrocortisone. Endothelial differentiation can be confirmed by expression of E-selectin (CD62E) and ICAM-2 (CD102).

MLPC can be induced to differentiate into cells having a hepatocyte/pancreatic precursor cell phenotype using an induction medium (e.g., HCM™-hepatocyte culture medium, catalog # CC-3198, from Cambrex) containing ascorbic acid, hydrocortisone, transferrin, insulin, EGF, hepatocyte growth factor, FGF-basic, fibroblast growth factor-4, and stem cell factor. Liver and pancreas cells share a common progenitor. Hepatocyte differentiation can be confirmed by expression of hepatocyte growth factor and human serum albumin. Pancreatic cell differentiation can be confirmed by production of insulin and pro-insulin.

Modified Populations of MLPC

MLPC can be modified such that the cells can produce one or more polypeptides or other therapeutic compounds of interest. To modify the isolated cells such that a polypeptide or other therapeutic compound of interest is produced, the appropriate exogenous nucleic acid must be delivered to the cells. In some embodiments, the cells are transiently transfected, which indicates that the exogenous nucleic acid is episomal (i.e., not integrated into the chromosomal DNA). In other embodiments, the cells are stably transfected, i.e., the exogenous nucleic acid is integrated into the host cell's chromosomal DNA. The term "exogenous" as used herein with reference to a nucleic acid and a particular cell refers to any nucleic acid that does not originate from that particular cell as found in nature. In addition, the term "exogenous" includes a naturally occurring nucleic acid. For example, a nucleic acid encoding a polypeptide that is isolated from a human cell is an exogenous nucleic acid with respect to a second human cell once that nucleic acid is introduced into the second human cell. The exogenous nucleic acid that is delivered typically is part of a vector in which a regulatory element such as a promoter is operably linked to the nucleic acid of interest.

Cells can be engineered using a viral vector such as an adenovirus, adeno-associated virus (AAV), retrovirus, lentivirus, vaccinia virus, measles viruses, herpes viruses, or bovine papilloma virus vector. See, Kay et al. (1997) Proc. Natl. Acad. Sci. USA 94:12744-12746 for a review of viral and non-viral vectors. A vector also can be introduced using mechanical means such as liposomal or chemical mediated uptake of the DNA. For example, a vector can be introduced into an MLPC by methods known in the art, including, for example, transfection, transformation, transduction, electroporation, infection, microinjection, cell fusion, DEAE dextran, calcium phosphate precipitation, liposomes, LIPOFECTIN™, lysosome fusion, synthetic cationic lipids, use of a gene gun or a DNA vector transporter.

A vector can include a nucleic acid that encodes a selectable marker. Non-limiting examples of selectable markers include puromycin, adenosine deaminase (ADA), aminoglycoside phosphotransferase (neo, G418, APH), dihydrofolate reductase (DHFR), hygromycin-B-phosphtransferase, thymidine kinase (TK), and xanthin-guanine phosphoribosyltransferase (XGPRT). Such markers are useful for selecting stable transformants in culture.

MLPC also can have a targeted gene modification. Homologous recombination methods for introducing targeted gene modifications are known in the art. To create a homologous recombinant MLPC, a homologous recombination vector can be prepared in which a gene of interest is flanked at its 5' and 3' ends by gene sequences that are endogenous to the genome of the targeted cell, to allow for homologous recombination to occur between the gene of interest carried by the vector and the endogenous gene in the genome of the targeted cell. The additional flanking nucleic acid sequences are of sufficient length for successful homologous recombination with the endogenous gene in the genome of the targeted cell. Typically, several kilobases of flanking DNA (both at the 5' and 3' ends) are included in the vector. Methods for constructing homologous recombination vectors and homologous recombinant animals from recombinant stem cells are commonly known in the art (see, e.g., Thomas and Capecchi, 1987, Cell 51:503; Bradley, 1991, Curr. Opin. Bio/Technol. 2:823-29; and PCT Publication Nos. WO 90/11354, WO 91/01140, and WO 93/04169.

Methods of Using MLPC

The MLPC can be used in enzyme replacement therapy to treat specific diseases or conditions, including, but not limited to lysosomal storage diseases, such as Tay-Sachs, Niemann-Pick, Fabry's, Gaucher's, Hunter's, and Hurler's syndromes, as well as other gangliosidoses, mucopolysaccharidoses, and glycogenoses.

In other embodiments, the cells can be used as carriers in gene therapy to correct inborn errors of metabolism, adrenoleukodystrophy, cystic fibrosis, glycogen storage disease, hypothyroidism, sickle cell anemia, Pearson syndrome, Pompe's disease, phenylketonuria (PKIJ), porphyrias, maple syrup urine disease, homocystinuria, mucoplysaccharidenosis, chronic granulomatous disease and tyrosinemia and Tay-Sachs disease or to treat cancer, tumors or other pathological conditions.

MLPC can be used to repair damage of tissues and organs resulting from disease. In such an embodiment, a patient can be administered a population of MLPC to regenerate or restore tissues or organs which have been damaged as a consequence of disease. For example, a population of MLPC can be administered to a patient to enhance the immune system following chemotherapy or radiation, or to repair heart tissue following myocardial infarction.

The cells also can be used in tissue regeneration or replacement therapies or protocols, including, but not limited to treatment of corneal epithelial defects, cartilage repair, facial dermabrasion, mucosal membranes, tympanic membranes, intestinal linings, neurological structures (e.g., retina, auditory neurons in basilar membrane, olfactory neurons in olfactory epithelium), burn and wound repair for traumatic injuries of the skin, or for reconstruction of other damaged or diseased organs or tissues.

MLPC also can be used in therapeutic transplantation protocols, e.g., to augment or replace stem or progenitor cells of the liver, pancreas, kidney, lung, nervous system, muscular system, bone, bone marrow, thymus, spleen, mucosal tissue, gonads, or hair.

Compositions and Articles of Manufacture

The invention also features compositions and articles of manufacture containing purified populations of MLPC or clonal lines of MLPC. In some embodiments, the purified population of MLPC or clonal line is housed within a container (e.g., a vial or bag). In some embodiments, the clonal lines have undergone at least 3 doublings in culture (e.g., at least 4, 5, 6, 7, 8, 9, 10, 15, 20, 25, 30, 35, 40, 45, or 50 doublings). In other embodiments, a culture medium (e.g., MSCGM™ medium) is included in the composition or article of manufacture. In still other embodiments, the composition or article of manufacture can include one or more cryopreservatives or pharmaceutically acceptable carriers. For example, a composition can include serum and DMSO, a mixture of serum, DMSO, and trehalose, or a mixture of human serum albumin, DMSO, and trehalose.

Purified populations of MLPC or clonal MLPC lines can be combined with packaging material and sold as a kit. The packaging material included in a kit typically contains instructions or a label describing how the purified populations of MLPC or clonal lines can be grown, differentiated, or used. Components and methods for producing such kits are well known.

The invention is further described in the following examples, which do not limit the scope of the invention described in the claims.

EXAMPLES

Example 1

Separating Blood Cells

This example describes the general method by which cells were separated using the cell separation reagents described below. Equal volumes of a cell separation reagent (see Table 1) and an acid citrate dextrose (ACD), CPDA (citrate, phosphate, dextrose, adenine) or heparinized umbilical cord blood sample were combined (25 ml each) in a sterile closed container (e.g., a 50 ml conical tube). Samples containing white blood cell counts greater than $20 \times 10^6$ cells/ml were combined one part blood with two parts cell separation reagent. Tubes were gently mixed on a rocker platform for 20 to 45 minutes at room temperature. Tubes were stood upright in a rack for 30 to 50 minutes to permit agglutinated cells to partition away from unagglutinated cells, which remained in solution. A pipette was used to recover unagglutinated cells from the supernatant without disturbing the agglutinate. Recovered cells were washed in 25 ml PBS and centrifuged at 500×g for 7 minutes. The cell pellet was resuspended in 4 ml PBS+2% human serum albumin.

TABLE 1

| Cell Separation Reagent | |
|---|---|
| Dextran (average molecular weight 413,000) | 20 g/l |
| Dulbecco's phosphate buffered saline (10X) | 100 ml/l |

TABLE 1-continued

| Cell Separation Reagent | |
|---|---|
| Sodium Heparin (10,000 units/ml) | 1 ml/l |
| Hank's balanced salt solution (pH 7.2-7.4) | 50 ml/l |
| Anti-human glycophorin A (murine IgM monoclonal antibody, clone 2.2.2.E7) | 0.1-15 mg/L (preferably about 0.25 mg/L) |
| Anti-CD15 (murine IgM monoclonal antibody, clone 324.3.B9) | 0.1-15 mg/L (preferably about 2.0 mg/L) |
| Anti-CD9 (murine IgM monoclonal antibody, clone 8.10.E7) | 0.1-15 mg/L (preferably about 2.0 mg/L) |

Cells also were recovered from the agglutinate using a hypotonic lysing solution containing EDTA and ethylene glycol-bis(2-aminoethylether)-N,N,N',N'-tetraacetic acid (EGTA). Agglutinated cells were treated with 25 ml VitaLyse® (BioE, St. Paul, Minn.) and vortexed. After 10 minutes, cells were centrifuged at 500×g for 7 minutes and the supernatant was removed. Cells were resuspended in 4 ml PBS.

Recoveries of erythrocytes, leukocytes, lymphocytes, monocytes, granulocytes, T cells, B cells, NK cells, hematopoietic stem cells, and non-hematopoietic stem cells were determined by standard flow cytometry and immunophenotyping. Prior to flow cytometry, leukocyte recovery (i.e., white blood cell count) was determined using a Coulter Onyx Hematology Analyzer. Cell types were identified and enumerated by combining hematology analysis with flow cytometry analysis, identifying cells on the basis of light scattering properties and staining by labeled antibodies.

As shown in Table 2, 99.9% of erythrocytes were removed, 99.8% monocytes and granulocytes, 74% of B cells, 64.9% of NK cells, and 99.4% of the platelets were removed from the cord blood.

TABLE 2

| | Recovery of Cells | |
|---|---|---|
| | Before separation | After separation |
| Erythrocytes per ml | $4.41 \times 10^9$ | $0.006 \times 10^9$ |
| Leukocytes per ml | $5.9 \times 10^6$ | $1.53 \times 10^6$ |
| Lymphocytes (%) | 28.7 | 99.0 |
| Monocytes (%) | 8.69 | 0.12 |
| Granulocytes (%) | 62.5 | .083 |
| T Cells (CD3+) | 19.7 | 83.2 |
| B Cells (CD19+) | 4.46 | 8.10 |
| NK Cells (CD16+) | 3.15 | 8.43 |
| Platelets per ml | $226 \times 10^6$ | $1.4 \times 10^6$ |

Example 2

Purification of MLPC

The cell separation reagent of Table 3 was used to isolate MLPC from the non-agglutinated supernatant phase. See FIG. 1 for a schematic of the purification.

TABLE 3

| Cell Separation Reagent | |
|---|---|
| Dextran (average molecular weight 413,000) | 20 g/l |
| Dulbecco's phosphate buffered saline (10X) | 100 ml/l |
| Sodium Heparin (10,000 units/ml) | 1 ml/l |

TABLE 3-continued

| Cell Separation Reagent | |
|---|---|
| Hank's balanced salt solution (pH 7.2-7.4) | 50 ml/l |
| Anti-human glycophorin A (murine IgM monoclonal antibody, clone 2.2.2.E7) | 0.1-15 mg/L (preferably about 0.25 mg/L) |
| Anti-CD15 (murine IgM monoclonal antibody, clone 324.3.B9) | 0.1-15 mg/L (preferably about 2.0 mg/L) |
| Anti-CD9 (murine IgM monoclonal antibody, clone 8.10.E7) | 0.1-15 mg/L (preferably about 2.0 mg/L) |

Briefly, 50-150 ml of CPDA anti-coagulated umbilical cord blood (<48 hours old) was gently mixed with an equal volume of cell separation composition described in Table 3 for 30 minutes. After mixing was complete, the container holding the blood/cell separation composition mixture was placed in an upright position and the contents allowed to settle by normal 1×g gravity for 30 minutes. After settling was complete, the non-agglutinated cells were collected from the supernatant. The cells were recovered from the supernatant by centrifugation then washed with PBS. Cells were resuspended in complete MSCGM™ (Mesenchymal stem cell growth medium, catalog # PT-3001, Cambrex, Walkersville, Md.) and adjusted to $2-9\times10^6$ cells/ml with complete MSCGM™. Cells were plated in a standard plastic tissue culture flask (e.g., Corning), chambered slide, or other culture device and allowed to incubate overnight at 37° C. in a 5% $CO_2$ humidified atmosphere. All subsequent incubations were performed at 37° C. in a 5% $CO_2$ humidified atmosphere unless otherwise noted. MLPC attached to the plastic during this initial incubation. Non-adherent cells (T-cells, NK-cells and CD34+ hematopoietic stem cells ) were removed by vigorous washing of the flask or well with complete MSCGM™.

MLPC cultures were fed periodically by removal of the complete MSCGM™ and addition of fresh complete MSCGM™. Cell were maintained at concentrations of $1\times10^5-1\times10^6$ cells 75 cm² by this method. When cell cultures reached a concentration of $8\times10^5-1\times10^6$ cells 75 cm², cells were cryopreserved using 10% DMSO and 90% serum or expanded into new flasks. Cells were recovered from the adherent cultures by removal of the complete MSCGM™ and replacement with PBS+0.1% EGTA. Cells were incubated for 15-60 minutes at 37° C. then collected from the flask and washed in complete MSCGM. Cells were then replated at $1\times10^5$ cells/mL. Cultures that were allowed to achieve confluency where found to have diminished capacity for both proliferation and differentiation. Subsequent to this finding, cultures were not allowed to achieve higher densities than $1\times10^6$ cells 75 cm².

Example 3

Morphology of MLPC and Development to Fibroblastic Morphology

Cord blood derived MLPC isolated and cultured according to Examples 1 and 2 were cultured in standard MSCGM™ until confluency. Depending on the donor, MLPC cultures achieved confluency in 2-8 weeks. The morphology of these cells during growth and cultural maturation is shown in FIG. 2A-2D.

In the early stage shown in FIG. 2A, the cells are dividing very slowly and resemble circulating leukocytes but with dendritic cytoplasmic extensions. Many cells still exhibit the small round cell morphology that these cells would exhibit in circulation. As culture continues, the leukocyte-like cells start to change their morphology from the leukocyte-like appearance to a flatter, darker more fibroblast-like appearance (see FIG. 2B). When cells are dividing, they round up, divide, and then reattach to the culture vessel surface and spread out again. This slowly continues until the cells fill the available surface. FIG. 2C shows the morphology of cell cultures during logarithmic growth. FIG. 2D shows the morphology of a fully confluent culture of MLPC. With the exception of the two cells in active division seen in the lower left corner of the picture, all of the cells have a fibroblast-like morphology.

In summary, early during culture, cells appeared small and round, but had cytoplasmic projections, both finger-like and highly elongate projections, which help distinguish them from the other blood cells. Shortly after the initiation of the culture, the cells began to spread and flatten, taking on a morphology consistent with fibroblasts. Eventually, upon confluency, the cells grew in largely parallel orientation. Repeated growth of cultures to confluency resulted in their having diminished proliferation and differentiating capacity.

Example 4

Immunophenotyping of Cells by Immunofluorescent Microscopy

In order to determine the surface markers present on MLPC, freshly isolated cells were plated in 16 well chamber slides and grown to confluency. At various times during the culture (from 3 days post plating to post confluency), cells were harvested and stained for the following markers: CD45-FITC (BD Pharmingen), CD34-PE (BD Pharmingen), CD4-PE (BioE), CD8-PE (BioE), anti-HLA-DR-PE (BioE), CD41-PE (BioE), CD9-PE (Ancell), CD105-PE (Ancell), CD29-PE (Coulter), CD73-PE (BD Pharmingen), CD90-PE (BD Pharmingen), anti-hu Stem Cell Factor-FITC (R&D Systems), CD14-PE (BD Pharmingen), CD15-FITC (Ancell), CD38-PE (BD Pharmingen), CD2-PE (BD Pharmingen), CD3-FITC (BD Pharmingen), CD5-PE (BD Pharmingen), CD7-PE (BD Pharmingen), CD16-PE (BD Pharmingen), CD20-FITC (BD Pharmingen), CD22-FITC (BD Pharmingen), CD19-PE (BD Pharmingen), CD33-PE (BD Pharmingen), CD10-FITC (BD Pharmingen), CD61-FITC (BD Pharmingen), CD133-PE (R&D Systems), anti-STRO-1 (R&D Systems) and Goat anti-mouse IgG(H+L)-PE (BioE), SSEA-3 (R&D Systems) and goat anti-rat IgG (H+L)-PE (BioE), SSEA-4 (R&D Systems) and goat anti-mouse IgG(H+L)-PE (BioE). The cell surface markers also were assessed in bone marrow MSC (Cambrex, Walkersville, Md.) and cord blood HSC (obtained from the non-adherent cells described above).

Briefly, cell culture medium was removed from the wells and the cells were washed 3× with Hank's Balanced Salt Solution+2% BSA. Cells were then stained with the antibodies for 20 minutes in the dark at room temperature. After incubation, the cells were washed 3× with Hank's Balanced Salt Solution+2% BSA and the cells were directly observed for fluorescence by fluorescent microscopy. Results obtained comparing cord blood derived MLPC with bone marrow-derived MSC's and cord blood derived-hematopoietic stem cells (HSC) are outlined in Table 4.

TABLE 4

| Cell Marker | Early MLPC (Leukocyte morphology) | Mature MLPC (Fibroblast morphology) | Cord Blood HSC | Bone Marrow MSC |
|---|---|---|---|---|
| CD2 | Negative | Negative | Negative | Negative |
| CD3 | Negative | Negative | Negative | Negative |
| CD4 | Negative | Negative | Negative | Negative |
| CD5 | Negative | Negative | Negative | Negative |
| CD7 | Negative | Negative | Negative | Negative |
| CD8 | Negative | Negative | Negative | Negative |
| CD9 | Positive | Positive | Negative | Negative |
| CD10 | Negative | Negative | Negative | Negative |
| CD13 | Positive | Positive | Negative | Positive |
| CD14 | Negative | Negative | Negative | Negative |
| CD15 | Negative | Negative | Negative | Negative |
| CD16 | Negative | Negative | Negative | Negative |
| CD19 | Negative | Negative | Negative | Negative |
| CD20 | Negative | Negative | Negative | Negative |
| CD22 | Negative | Negative | Negative | Negative |
| CD29 | Positive | Positive | Positive | Positive |
| CD33 | Negative | Negative | Variable | Negative |
| CD34 | Positive | Negative | Positive | Negative |
| CD36 | Negative | Negative | Negative | Negative |
| CD38 | Negative | Negative | Variable | Negative |
| CD41 | Negative | Negative | Negative | Negative |
| CD45 | Positive | Negative | Positive | Negative |
| CD61 | Negative | Negative | Variable | Negative |
| CD73 | Positive | Positive | Negative | Positive |
| Anti-HLA-DR | Negative | Negative | Variable | Negative |
| CD90 | Positive | Positive | Positive | Positive |
| CD105 | Positive | Positive | Negative | Positive |
| STRO-1 | Positive | Negative | Negative | Negative |
| SSEA-3 | Positive | Negative | Negative | Negative |
| SSEA-4 | Positive | Negative | Negative | Negative |
| SCF | Positive | Negative | Negative | Negative |
| Glycophorin A | Negative | Negative | Negative | Negative |
| CD133 | Positive | Negative | Positive | Negative |

Example 5

Clonal MLPC Cell Lines

After the second passage of MLPC cultures from Example 2, the cells were detached from the plastic surface of the culture vessel by substituting PBS containing 0.1% EGTA (pH 7.3) for the cell culture medium. The cells were diluted to a concentration of 1.3 cells ml in complete MSCGM™ and distributed into a 96 well culture plate at a volume of 0.2 ml/well, resulting in an average distribution of approximately 1 cell/3 wells. After allowing the cells to attach to the plate by overnight incubation at 37° C., the plate was scored for actual distribution. Only the wells with 1 cell well were followed for growth. As the cells multiplied and achieved concentrations of $1\text{-}5\times10^5$ cells 75 cm², they were transferred to a larger culture vessel in order to maintain the cells at a concentration between $1\times10^5$ and $5\times10^5$ cells 75 cm² to maintain logarithmic growth. Cells were cultured at 37° C. in a 5% $CO_2$ atmosphere.

At least 52 clonal cell lines have been established using this procedure and were designated: UM081704-1-E2, UM081704-1-B6, UM081704-1-G11, UM081704-1-G9, UM081704-1-E9, UM081704-1-E11, UM081704-1-G8, UM081704-1-H3, UM081704-1-D6, UM081704-1-H11, UM081704-1-B4, UM081704-1-H4, UM081704-1-C2, UM081704-1-G1, UM081704-1-E10, UM081704-1-B7, UM081704-1-G4, UM081704-1-F12, UM081704-1-H1, UM081704-1-D3, UM081704-1-A2, UM081704-1-B11, UM081704-1-D5, UM081704-1-E4, UM081704-1-C10, UMO81704-1-A5, UM081704-1-E8, UM081704-1-C12, UM081704-1-E5, UM081704-1-A12, UM081704-1-C5, UM081704-1-A4, UM081704-1-A3, MH091404-2 #1-1.G10, UM093004-1-A3, UM093004-1-B7, UM093004-1-F2, UM093004-1-A12, UM093004-1-G1, UM093004-1-G4, UM093004-1-B12, UM093004-2-A6, UM093004-2-A9, UM093004-2-B9, UM093004-2-C5, UM093004-2-D12, UM093004-2-H3, UM093004-2-H11, UM093004-2-H4, UM093004-2-A5, UM093004-2-C3, and UM093004-2-C10. The surface markers of clonal cell line UM081704-1-E8 were assessed according to the procedure outlined in Example 4 and found to be the same as the "mature MLPC" having fibroblast morphology, as shown in Table 4.

Example 6

Osteocytic Differentiation of MLPC

A population of MLPC and clonal cell line UM081704-1-E8 each were cultured in complete MSCGM™ and grown under logarithmic growth conditions outlined above. Cells were harvested by treatment with PBS+0.1% EGTA and replated at $5\times10^3$ to $2\times10^4$/ml in complete MSCGM™. The cells were allowed to adhere overnight and then the medium was replaced with Osteogenic Differentiation Medium (catalog #PT-3002, Cambrex,) consisting of complete MSCGM™ supplemented with dexamethasone, L-glutamine, ascorbate, and β-glycerophosphate. Cells were cultured at 37° C. in a 5% $CO_2$ atmosphere and fed every 3-4 days for 2-3 weeks. Deposition of calcium crystals was demonstrated by using a modification of the Alizarin red procedure and observing red staining of calcium mineralization by phase contrast and fluorescent microscopy.

Example 7

Adipocytic Differentiation of MLPC

A population of MLPC and clonal cell line UM081704-1-E8 each were plated in complete MSCGM™ at a concentration of $1\times10^4$ to $2\times10^5$ cells/mL medium and cultured at 37° C. in a 5% $CO_2$ atmosphere. Cells were allowed to re-adhere to the culture plate and were fed every 3-4 days until the cultures reached confluency. At 100% confluency, cells were differentiated by culture in Adipogenesis differentiation medium (catalog #PT-3004, Cambrex) consisting of complete MSCGM™ supplemented with hu-insulin, L-glutamine, dexamethasone, indomethacin, and 3-isobutyl-1-methyl-xanthine, for at least 14 days.

To assess differentiation, the cells were stained with Oil Red stain specific for lipid. Confluent cultures of MLPC display a fibroblast-like morphology and do not display any evidence of liposome development as assessed by Oil Red staining. In contrast, MLPC differentiated with Adipogenic medium for 3 weeks exhibit liposomes that are characteristic of adipocytes (i.e., bright white vessels in cytoplasm) and that stain red with the Oil Red stain. MLPC differentiated with Adipogenic medium also fluoresce green with Nile Red stain specific for trigycerides. Undifferentiated cells retain their fibroblast-like morphology and do not stain.

Example 8

Myocytic Differentiation of MLPC

MLPC (both a population and clonal cell line UM081704-1-E8) were plated in complete MSCGM™ at a concentration of $1.9\times10^4$ cells/well within a 4-chamber fibronectin pre-coated slide and allowed to attach to the plate for 24-48 hr at 37° C. in a 5% $CO_2$ atmosphere. Medium was removed and replaced with 10 μM 5-azacytidine (catalog #A1287, Sigma Chemical Co.) and incubated for 24 hours. Cells were washed twice with PBS and fed with SkGM™ Skeletal Muscle Cell Medium (catalog # CC-3160, Cambrex) containing recombinant human epidermal growth factor (huEGF), human insulin, Fetuin, dexamethasone, and recombinant human basic fibroblast growth factor (100 ng mL) (huFGF-basic, catalog # F0291, Sigma Chemical Co., St. Louis, Mo.). Cells were fed every 2-3 days for approximately 21 days. Control wells were fed with MSCGM™ while experimental wells were fed with SkGM™ (as described above).

Cultures were harvested 7 days post initiation of myocytic culture. Culture supernatant was removed and cells were fixed for 2 hours with 2% buffered formalin. Cells were permeabilized with PermaCyte™ (BioE, St. Paul, Minn.) and stained with mouse monoclonal antibody specific for human fast skeletal myosin (MY-32, catalog #ab7784, Abcam, Cambridge, Mass.) or mouse monoclonal antibody specific for alpha actinin (BM 75.2, catalog #ab11008, Abcam). Cells were incubated with the primary antibody for 20 minutes, washed with PBS and counter stained with goat anti-mouse IgG (H+L)-PE (BioE, St. Paul, Minn.). The myocytic culture contained fast skeletal muscle myosin and alpha actinin, which is indicative of the transdifferentiation of MLPC to skeletal muscle cells.

Example 9

Neurocytic Differentiation of MLPC

Bone marrow derived hMSC (Cambrex), cord blood MLPC, and MLPC clonal cell line were grown under logarithmic growth conditions described above. Cells were harvested as described above and replated at $0.8 \times 10^4$ cells per chamber in 4-chamber slides that were pre-coated with poly-D-lysine and laminin (BD Biosciences Discovery Labware, catalog #354688) in 0.5 mL of NPMM™ (catalog #CC-3209, Cambrex) containing huFGF-basic, huEGF, brain-derived neurotrophic factor, neural survival factor-1, fibroblast growth factor-4 (20 ng mL), and 200 mM GlutaMax I Supplement (catalog #35050-061, Invitrogen, Carlsbad, Calif.). The medium was changed every 2-3 days for 21 days. Neurospheres developed after 4 to 20 days. Transformation of MLPC to neural lineage was confirmed by positive staining for nestin (monoclonal anti-human nestin antibody, MAB1259, clone 196908, R&D Systems), class III beta-tubulin (tubulin b-4) (monoclonal anti-neuron-specific class III beta-tubulin antibody, MAB 1195, Clone TuJ-1, R&D Systems), glial fibrillary acidic protein (GFAP) (monoclonal anti-human GFAP, HG2b-GF5, clone GF5, Advanced Immunochemical, Inc.), and galactocerebroside (GalC) (mouse anti-human GalC monoclonal antibody MAB342, clone mGalC, Chemicon).

Cells were further differentiated into neurons by the addition of 10 ng mL BDNF (catalog #B3795, Sigma Chemical Co.) and 10 ng mL NT3 (catalog #N1905, Sigma Chemical Co.) to the neural progenitor maintenance medium and further culturing for 10-14 days. Neurospheres were further differentiated into astrocytes by the addition of $10^{-6}$ M retinoic acid (catalog #R2625, Sigma Chemical Co.), 10 ng mL LIF (catalog #L5158, Sigma Chemical Co.) and 10 ng mL CNTF (catalog #C3710, Sigma Chemical Co.) to the neural progenitor maintenance medium and further culturing for 10-14 days. Neurospheres were further differentiated into oligodendrocytes by the addition of $10^{-6}$ M T3 (catalog #T5516, Sigma Chemical Co.) to the neural progenitor maintenance medium and further culturing for 10- 14 days. Differentiation to oligodendrocytes was confirmed by positive staining for myelin basic protein (MBP) (monoclonal anti-MBP, catalog #ab8764, clone B505, Abcam).

Example 10

Endothelial Differentiation of MLPC

MLPC were plated at $1.9 \times 10^4$ cells per well within a 4-chamber slide (2 cm$^2$). Cells were fed with 1 ml of endothelial growth medium-microvasculature (EGM™-MV, catalog #CC-3125, Cambrex) containing heparin, bovine brain extract, human recombinant epithelial growth factor and hydrocortisone. The cells were fed by changing the medium every 2-3 days for approximately 21 days. Morphological changes occurred within 7-10 days. Differentiation of MLPC's to endothelial lineage was assessed by staining for CD62E [E-selectin, mouse anti-human CD62E monoclonal antibody, catalog #551145, clone 68-5H11, BD Pharmingen] and CD102 [ICAM-2, monoclonal anti-human ICAM-2, MAB244, clone 86911, R&D Systems]. Control MLPC cultures grown in MSCGM for 14 days were negative for CD62E staining and CD102, while differentiated cultures were positive for both CD62E and CD102.

Example 11

Differentiation of MLPC into Hepatocyte/Pancreatic Precursor Cells

MLPC were plated at a concentration of $1 \times 10^5$ cells cm$^2$ in vitro in HCM™ medium (catalog #CC-3198, Cambrex) containing ascorbic acid, hydrocortisone, transferrin, insulin, huEGF, recombinant human hepatocyte growth factor (40 ng mL), huFGF-basic (20 ng mL), recombinant human fibroblast growth factor-4 (20 ng mL), and stem cell factor (40 ng mL). Cells were cultured for 29 or more days to induce differentiation to precursor cells of both hepatocytes and pancreatic cells lineage. MLPC changed from a fibroblast morphology to a hepatocyte morphology, expressed cell surface receptors for Hepatocyte Growth Factor, and produced both human serum albumin, a cellular product of hepatocytes, and insulin, a cellular product of pancreatic islet cells, both confirmed by intracellular antibody staining on day 30.

Other Embodiments

While the invention has been described in conjunction with the foregoing detailed description and examples, the foregoing description and examples are intended to illustrate and not to limit the scope of the invention, which is defined by the scope of the appended claims. Other aspects, advantages, and modifications are within the scope of the claims.

What is claimed is:

1. A purified population of human fetal blood multi-lineage progenitor cells (MLPC), wherein said MLPC are positive for CD9, CD13, CD29, CD44, CD73, CD90 and CD105, and negative for CD10, CD34, CD41, CD45, Stro-1, Stage Specific Embryonic Antigen-3 (SSEA-3) and SSEA-4.

2. The purified population of MLPC of claim 1, wherein said MLPC display a fibroblast morphology.

3. The purified population of MLPC of claim 1, wherein said MLPC are obtained from cord blood.

4. The purified population of MLPC of claim 1, wherein said MLPC are further negative for CD2, CD3, CD4, CD5, CD7, CD8, CD14, CD15, CD16, CD19, CD20, CD22, CD33, CD36, CD38, CD61, CD62E, CD133, glycophorin-A, stem cell factor, and HLA-DR.

5. The purified population of MLPC of claim 1, wherein said MLPC adhere to a plastic surface when cultured.

6. The purified population of MLPC of claim 1, wherein said MLPC are capable of differentiating into cells from all three embryonic germ layers.

7. The purified population of MLPC of claim 6, wherein said MLPC are capable of differentiating into cells having an osteocytic phenotype, cells having an adipocytic phenotype, cells having a neural stem cell phenotype, cells having a myocytic phenotype, cells having an endothelial phenotype, cells having a hepatocyte precursor phenotype, and cells having a pancreatic precursor phenotype.

8. The purified population of MLPC of claim 1, wherein said MLPC comprise an exogenous nucleic acid.

9. The purified population of MLPC of claim 8, wherein said exogenous nucleic acid encodes a polypeptide.

10. A clonal line of human fetal blood MLPC, wherein MLPC are positive for CD9, CD13, CD29, CD44, CD73, CD90 and CD105, and negative for CD10, CD34, CD41, CD45, Stro-1, SSEA-3 and SSEA-4.

11. The clonal line of claim 10, wherein said MLPC display a fibroblast morphology.

12. The clonal line of claim 10, wherein said MLPC are obtained from cord blood.

13. The clonal line of claim 10, wherein said MLPC are further negative for CD2, CD3, CD4, CD5, CD7, CD8, CD14, CD15, CD16, CD19, CD20, CD22, CD33, CD36, CD38, CD61, CD62E, CD133, glycophorin-A, stem cell factor, and HLA-DR.

14. The clonal line of claim 10, wherein said MLPC adhere to a plastic surface when cultured.

15. The clonal line of claim 10, wherein said MLPC are capable of differentiating into cells from all three embryonic germ layers.

16. The clonal line of claim 15, wherein said MLPC are capable of differentiating into cells having an osteocytic phenotype, cells having an adipocytic phenotype, cells having a neural stem cell phenotype, cells having a myocytic phenotype, cells having an endothelial phenotype, cells having a hepatocyte precursor phenotype, and cells having a pancreatic precursor phenotype.

17. The clonal line of claim 10, wherein said MLPC comprise an exogenous nucleic acid.

18. The clonal line of claim 17, wherein said exogenous nucleic acid encodes a polypeptide.

19. The clonal line of claim 10, wherein said MLPC have undergone at least 30 doublings in culture.

20. The clonal line of claim 10, wherein said MLPC have undergone at least 35 doublings in culture.

21. The clonal line of claim 10, wherein said MLPC have undergone at least 40 doublings in culture.

22. The clonal line of claim 10, wherein said MLPC have undergone at least 50 doublings in culture.

23. An article of manufacture comprising the purified population of MLPC of claim 14, or the clonal line of claim 10.

24. The article of manufacture of claim 23, wherein said purified population of MLPC or said clonal line is housed within a container.

25. The article of manufacture of claim 24, wherein said container is a vial.

26. The article of manufacture of claim 24, wherein said container is a bag.

27. A purified population of MLPC, wherein said MLPC are made by the following method:
 a) contacting a human fetal blood sample with a composition, said composition comprising:
  i) dextran;
  ii) anti-glycophorin A antibody;
  iii) anti-CD15 antibody; and
  iv) anti-CD9 antibody;
 b) allowing said sample to partition into an agglutinate and a supernatant phase;
 c) recovering cells from said supernatant phase;
 d) purifying MLPC from the recovered cells by adherence to a solid substrate; and
 e) culturing said MLPC such that said MLPC obtain a fibroblast morphology, wherein said MLPC, after obtaining said fibroblast morphology, are positive for CD9, CD13, CD29, CD44, CD73, CD90 and CD105, and negative for CD10, CD34, CD41, CD45, Stro-1, SSEA-3, and SSEA-4.

28. The purified population of MLPC of claim 27, wherein said MLPC are obtained from cord blood.

29. The purified population of MLPC of claim 27, wherein said MLPC are further negative for CD2, CD3, CD4, CD5, CD7, CD8, CD14, CD15, CD16, CD19, CD20, CD22, CD33, CD36, CD38, CD61, CD62E, CD133, glycophorin-A, stem cell factor, and HLA-DR.

30. The purified population of MLPC of claim 27, wherein said MLPC are capable of differentiating into cells from all three embryonic germ layers.

31. The purified population of MLPC of claim 30, wherein said MLPC are capable of differentiating into cells having an osteocytic phenotype, cells having an adipocytic phenotype, cells having a neural stem cell phenotype, cells having a myocytic phenotype, cells having an endothelial phenotype, cells having a hepatocyte precursor phenotype, and cells having a pancreatic precursor phenotype.

32. A clonal line of MLPC, wherein said clonal line is made by the following method:
 a) culturing a single MLPC in a culture vessel lacking other cells until a plurality of progeny are produced; and
 b) culturing said progeny to obtain said clonal line of MLPC, wherein said MLPC are positive for CD9, CD13, CD29, CD44, CD73, CD90 and CD105, and negative for CD10, CD34, CD41, CD45, Stro-1, SSEA-3, and SSEA-4.

33. The clonal line of claim 32, wherein said MLPC are obtained from cord blood.

34. The clonal line of claim 32, wherein said MLPC are further negative for CD2, CD3, CD4, CD5, CD7, CD8, CD14, CD15, CD16, CD19, CD20, CD22, CD33, CD36, CD38, CD61, CD62E, CD133, glycophorin-A, stem cell factor, and HLA-DR.

35. The clonal line of claim 32, wherein said MLPC are capable of differentiating into cells from all three embryonic germ layers.

36. The clonal line of claim 35, wherein said MLPC are capable of differentiating into cells having an osteocytic phenotype, cells having an adipocytic phenotype, cells having a neural stem cell phenotype, cells having a myocytic phenotype, cells having an endothelial phenotype, cells having a hepatocyte precursor phenotype, and cells having a pancreatic precursor phenotype.

* * * * *